(12) United States Patent
Guerry et al.

(10) Patent No.: US 9,308,246 B2
(45) Date of Patent: Apr. 12, 2016

(54) **CAPSULE COMPOSITION FOR USE AS IMMUNOGEN AGAINST *CAMPYLOBACTER JEJUNI***

(75) Inventors: Patricia Guerry, Silver Spring, MD (US); Mario Artur Monteiro, Guelph (CA)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 642 days.

(21) Appl. No.: 13/117,215

(22) Filed: May 27, 2011

(65) Prior Publication Data

US 2011/0300173 A1     Dec. 8, 2011

Related U.S. Application Data

(60) Provisional application No. 61/349,355, filed on May 28, 2010.

(51) Int. Cl.
*A61K 39/02* (2006.01)
*A61K 38/00* (2006.01)
*C07H 1/00* (2006.01)
*A61K 39/00* (2006.01)

(52) U.S. Cl.
CPC ....... *A61K 39/105* (2013.01); *A61K 2039/6037* (2013.01); *A61K 2039/627* (2013.01)

(58) Field of Classification Search
None
See application file for complete search history.

(56) References Cited

U.S. PATENT DOCUMENTS 5,869,066 A * 2/1999 Pace et al. ............ 424/282.1
7,598,354 B2   10/2009 Young et al.
7,700,578 B2   4/2010 Guerry et al.
2007/0065461 A1   3/2007 Guerry et al.
2009/0004223 A1 * 1/2009 Guerry et al. ........... 424/234.1
2010/0216185 A1   8/2010 Wakarchuk et al.

OTHER PUBLICATIONS

Chen et al. (2008; The chemical structure and genetic locus of Campylobacter jejuni CG8486 (serotype HS:4) capsular polysaccharide: the identification of 6-deoxy-D-ido-heptopyranose, Carbohydrate Research 343:1034-1040).*
McNally et al. (2006; the HS:19 serostrain of Campylobacter jejuni has a hyaluronic acid-type capsular polysaccharide with a nonstoichiometric sorbose brand and O-methyl phosphoramidate group, FEBS Journal 273:3975-3989).*
Monteiro et al. 2009 (Capsule polysaccharide conjugate vaccine against diarrheal disease caused by Campylobacter jejuni, Infection and Immunity, 77(3):1128-1136).*
Takahashi et al. 2005 (Epidemiology of Campylobacter jejuni isolated from patients with Guillain-Barre and Fisher Syndromes in Japan; Journal of clinical microbiology, 43(1):335-339).*
Monteiro et al. 2009; Infection and Immunity, 77(3):1128-1136.*
Chen et al. 2008; Carbohydrate Research, 343: 1034-1040.*
McNally et al. 2006; FEBS Journal 273: 3975-3989.*
Guerry et al. 2012 (Campylobacter polysaccharide capsules: virulence and vaccines; Cellular and Infection Microbiology 2:1-11).*
Hannify, et al. Chemical structure of a polysaccharide from Campylobacter jejuni 176.83 (serotype 0:41) containing only furanose sugars, Carbohydrate Research (1999) vol. 310 (1-4): pp. 124-132; p. 124, col. 2, para 1; p. 130, col. 2, para 2; abstract. Applied to claims 1-16.
Poly, et al. Discrimination of Major Capsular Types of Campylobacter jejuni by Multiplex PCR, J Clin Microbial (2011) vol. 49: pp. 1750-1757; p. 1753, col. 1, para 3. Applied to claims 1-16.

* cited by examiner

*Primary Examiner* — Gary Nickol
*Assistant Examiner* — Mary Lyons
(74) *Attorney, Agent, or Firm* — Albert M. Churilla; Ning Yang; Diane Tso

(57) ABSTRACT

Immunogenic compositions, and method of using the compositions to elicit an immune response against *Campylobacter jejuni*. The compositions are isolated polysaccharide polymers derived from *Campylobacter jejuni* capsule.

11 Claims, 14 Drawing Sheets

Campylobacter jejuni HS:15

Campylobacter jejuni HS:10

US 9,308,246 B2

CAPSULE COMPOSITION FOR USE AS IMMUNOGEN AGAINST *CAMPYLOBACTER JEJUNI*

CROSS-REFERENCE TO RELATED APPLICATIONS

Figure 1:
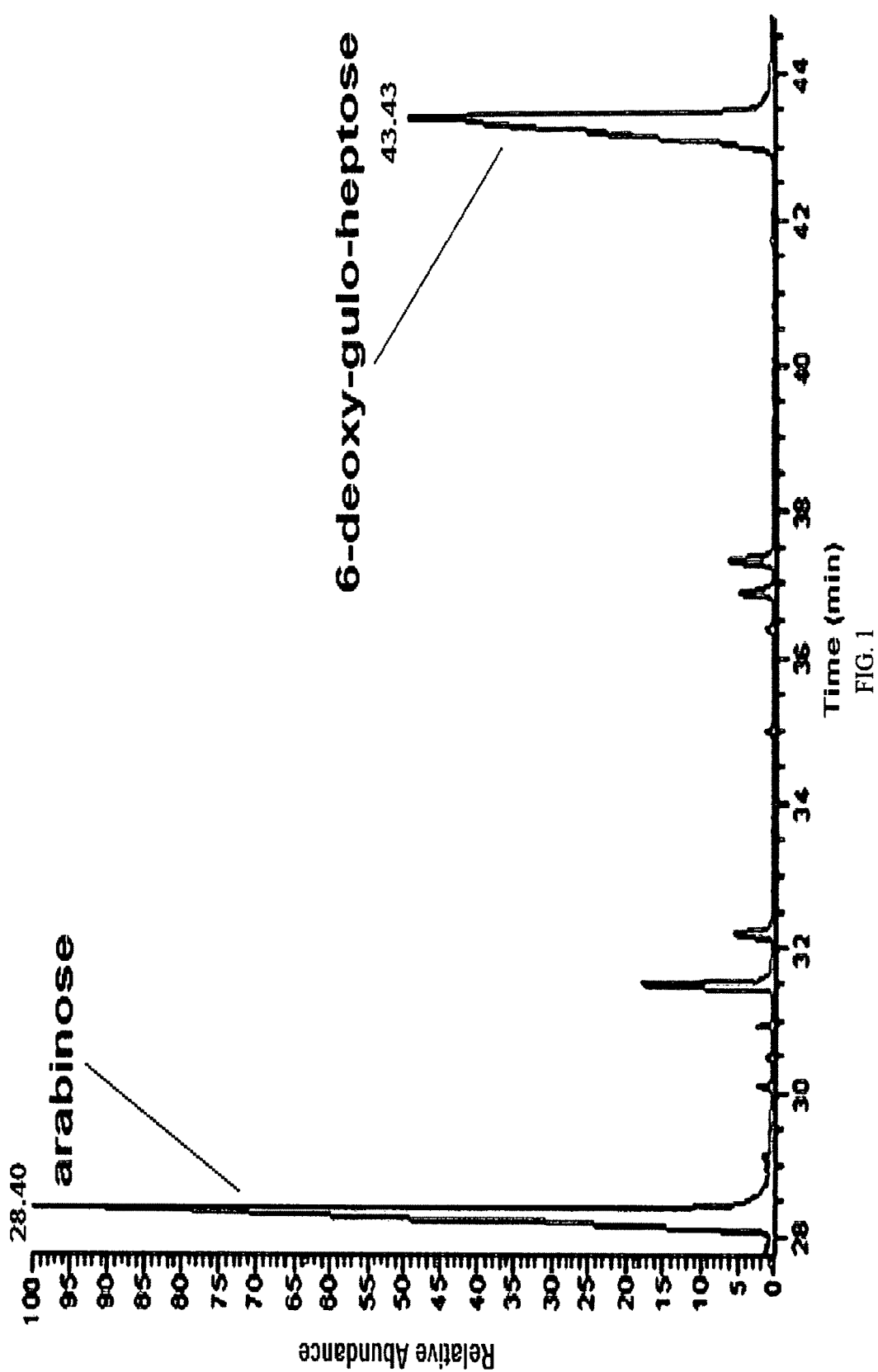

This application claims the benefit of U.S. Provisional Application No. 61/349,355, filed May 28, 2010, which is incorporated herein by reference.

FEDERALLY SPONSORED RESEARCH

This invention was made with government support under grant 1U01A1082105-01 awarded by the National Institute of Allergy and Infectious Diseases. The Government has certain rights.

JOINT RESEARCH AGREEMENT

The subject matter of the claimed invention was made by or on behalf of parties to a joint research agreement (i.e., NIAID grant number 1U01A1082105-01). The parties to the agreement are Patricia Guerry (U.S. Navy/Naval Medical Research Center, Silver Spring, Md.) and Mario Monteiro (University of Guelph, Guelph, Ontario, Canada).

FIELD OF THE INVENTION

The inventive subject matter relates to an immunogenic composition capable of conferring protection against diarrhea caused by *Campylobacter jejuni* and a method of inducing an immune response to said composition.

BACKGROUND OF INVENTION

*C. jejuni* is a leading cause of diarrheal disease worldwide and a documented threat to US military personnel (Taylor, Current status and future trends. Amer. Soc. Micro., (1992); Tauxe, Current status and future trends. Amer. Soc. Micro. 1992). The symptoms of *campylobacter* enteritis include diarrhea, abdominal pain, and fever and often accompanied by vomiting. Stools usually contain mucus, fecal leukocytes, and blood, although watery diarrhea is also observed (Cover and Blaser, Ann. Rev. Med., 40: 269-285 (1999). However, despite the importance of this organism to human disease, there are no licensed vaccines against *C. jejuni*.

Because of the medical importance of *C. jejuni*, considerable research is dedicated toward understanding the pathogen. However, notwithstanding this effort, there is surprisingly little understanding about how *C. jejuni* causes human disease. The genome of one strain, NCTC 11168 (Parkhill, et al., Nature, 403: 665-668 (2000) revealed several unusual aspects about the biology of *C. jejuni*. One striking feature is the presence of an unexpectedly high number of genes encoding putative enzymes involved in sugar and/or polysaccharide synthesis (Parkhill et al., Nature, 403: 665-668 (2000). The sequence, and resulting research fostered primarily by the availability of the sequence, has revealed that these genes fall into 4 main functional clusters that underscore the importance of some unusual carbohydrate structure to the biology of *C. jejuni*. These clusters include Lipooligosaccharide (LOS) synthesis, genetic control of flagellin glycosylation, genetic control of N-linked glycosylation, and the control of the biosynthesis and assembly of capsule.

Vaccine strategies against *C. jejuni* have been largely limited due to the molecular mimicry between lipooligosaccharide (LOS) cores of many strains of *C. jejuni* and human gangliosides (Moran, et al., J. Endotox. Res., 3: 521-531 (1996). This mimicry is thought to be a major factor in the strong association of *C. jejuni* infection with Guillain Barre Syndrome (GBS), a post-infectious polyneuropathy (Allos, J. Infect. Dis., 176(Suppl.): S125-128 (1997)). Thus, antibodies generated against LOS cores result in an autoimmune response to human neural tissue. It has been estimated that as many as 1/3000 cases of *campylobacter* enteritis results in GBS. Therefore, the possibility of developing GBS could be associated with any whole cell vaccine against *C. jejuni* that includes ganglioside mimicry.

LOS synthesis in *Campylobacter* is controlled by a number of genes, including genes encoding enzymes involved in biosynthesis of sialic acid for incorporation into LOS. Thus, *C. jejuni* is one of a limited number of bacteria that can endogenously synthesize sialic acid, a 9 carbon sugar that is found in many mammalian cells. This is consistent with the observed molecular mimicry of LOS and human gangliosides important in GBS (Aspinall, et al., Eur. J. Biochem., 213: 1029-1037 (1993); Aspinall, et al., Infect. Immun. 62: 2122-2125 (1994); Aspinall, et al., Biochem., 33: 241-249 (1994); Salloway et al., Infect. Immun., 64: 2945-2949 (1996)).

Although glycosylation of proteins was once considered to be a eukaryotic trait, there is an increase awareness of prokaryotic protein glycosylation (Power and Jennings, FEMS Microbiol. Lett., 218: 211-222 (2003); Ewing, et al., J. Bacteriol. 191:7086 (2009)). The best characterized and most extensively glycosylated bacterial protein is *campylobacter* flagellin. Flagellin from strain 81-176 is glycosylated at 19 serine or threonine sites by an O-linkage to pseudaminic acid and derivatives of pseudaminic acid (Thibault et al., J. Biol. Chem., 276: 34862-34870 (2001)). Pseudaminic acid is an unusual 9 carbon sugar that resembles sialic acid, but which is highly immunogenic, unlike sialic acid. Moreover, mutants that are unable to glycosylate flagellin cannot assemble a flagellar filament (Goon et al, Mol. Microbiol., 50: 659-671 (2003)). Since flagella are indispensable virulence determinants of *C. jejuni*, glycosylation is therefore also a key virulence determinant.

One of the most unusual aspects of *C. jejuni* is the presence of a general system for N-linked glycosylation of numerous proteins (Szymanski et al., Mol. Microbiol., 32: 1022-1030 (1999)); reviewed in Szymanski et al., Trends Microbiol., 11: 233-238 (2003). This system, which includes an oligosaccharide transferase similar to that found in the eukaryote *Saccharomyces cerevisiae*, attaches a glycan which has recently been shown to be a heptasaccharide composed of one bacillosamine residue (an unusual deoxy sugar), one D-glucose, and five D-GalNAc residues (Young et al., J. Biol. Chem., 277: 42530-42539 (2002)). The glycosylation appears to occur on numerous periplasmic, and perhaps, surface exposed proteins in *C. jejuni* (Young et al., J. Biol. Chem., 277: 42530-42539 (2002)). The unusual glycan, again, appears to be highly immunogenic and is recognized during human infection (Szymanski et al., Mol. Microbiol., 32: 1022-1030 (1999); Szymanski et al., Trends Microbiol., 11: 233-238 (2003)).

An interesting recent revelation regarding the *Campylobacter* genome sequence was the presence of a complete set of capsule transport genes similar to those seen in type II/III capsule loci in the Enterobactericeae (Parkhill et al., Nature, 403: 665-668 (2000); Karlyshev et al., Mol. Microbiol., 35: 529-541 (2000)). Subsequent genetic studies in which site-specific mutations were made in several capsule transport genes indicated that the capsule was the serodeterminant of the Penner serotyping scheme (Karlyshev et al., Mol. Microbiol., 35: 529-541 (2000)). The Penner scheme (or HS for heat stable) is one of two major serotyping schemes of campylobacters and was originally thought to be based on lipopolysaccharide O side chains (Moran and Penner, J. Appl. Microbiol., 86: 361-377 (1999)).

Currently it is believed that the structures previously described as O side chains are, in fact, capsules. The chemical structures of the capsule/O side chains of several Penner serotypes have been determined, and these structures include several unusual sugar structures, as summarized in Table 1.

ride antigens are considered to be T cell independent, and capable of inducing only IgM type responses. Adult humans, in contrast, are able to generate IgG, in addition to IgM and IgA antibodies against polysaccharides. Responses in infants to vaccines against type B *H. influenzae* (Schneerson et al., J. Exp. Med. 152: 361-376 (1980); Anderson, P. W., Infect. Immun., 39: 233-238 (1983); Marburg, et al., J. Am. Chem. Soc., 108: 5282-5287 (1986)), group A, B and C *Neisseria meningiditis* (Jennings and Lugowski, J. Immunol., 127: 1011-1018 (1981); and Jennings, et al., Carbohydr. Res., 112:

TABLE 1

Structure of some capsular polysaccharides of *C. jejuni* strains.

| Strain | Structure | Reference |
|---|---|---|
| HS3 | →4-α-D-Gal-(1→3)(3-hydroxypropanoyl)-L-glycero-α-D-ido-Hep-(1→ | Aspinall et al., 1995 |
| HS19 | →4)-β-D-GlcA-(1→3)-β-D-GlcNAc-(1→<br>(the GlcA units are present as amides of 2-amino-2-deoxyglycerol) | Aspinall et al., 1994 a, b |
| HS23, HS36 | Four closely-related polysaccharides:<br>→3)-β-D-GlcNAc-(1→3)-α-D-Gal-(1→2)-6d-α-D-altro-Hep-(1→;<br>→3)-β-D-GlcNAc-(1→3)-α-D-Gal-(1→2)-6d-3-O—Me-α-D-altro-Hep-(1→;<br>→3)-β-D-GlcNAc-(1→3)-α-D-Gal-(1→2)-D-glycero-α-D-altro-Hep-(1→;<br>→3)-β-D-GlcNAc-(1→3)-α-D-Gal-(1→2)-3-O—Me-D-glycero-α-D-altro-Hep-(1→ | Aspinall et al., 1992 |
| 81116 | Two polysaccharides at a ratio of 3A:1B, where<br><br>$\quad\quad\quad\quad\quad$ OAc (30%) $\quad\quad\quad\quad$ OAc (20%)<br>$\quad\quad\quad\quad\quad\quad\quad\downarrow\quad\quad\quad\quad\quad\quad\quad\quad\downarrow$<br>$\quad\quad\quad\quad\quad\quad\quad 3\quad\quad\quad\quad\quad\quad\quad\quad 6$<br>A = →3)-β-D-Glc-(1→2)-α-D-GlcA-(1→3)-α-D-Man-(1→3)-α-D-GlcA-(1→<br>B = →3)-β-D-GlcNAc-(1→6)-α-D-Glc-(1→4)-α-D-Gal-(1→<br>$\quad\quad\quad\quad\quad\quad\quad\quad\quad\quad\quad\quad\quad\quad\quad 3$<br>$\quad\quad\quad\quad\quad\quad\quad\quad\quad\quad\quad\quad\quad\quad\quad\uparrow$<br>$\quad\quad\quad\quad\quad\quad\quad\quad\quad\quad\quad\quad$ β-D-GlcNAc-(1 | Muldoon et al. (2002) |
| NCTC11168 | 6-O-Me-D-L-α-L-glc-Hepp-(1<br>$\quad\quad\quad\quad\quad\quad\quad\downarrow$<br>→2-β-D-Ribf-(1→5)-β-D-GalfNAc-(1→4)-α-D-GlcpA6(NGro)-(1→<br>(Here, Glucuronic acid is amidated with 2-amino-2-deoxyglycerol at C-6) | St. Michael et al. (2002) |

There currently are no licensed vaccines against *Campylobacter*, due greatly to the molecular mimicry between LOS cores of many strains of *C. jejuni* and human gangliosides (Moran, et al., J. Endotox. Res., 3: 521-531 (1996)). However, vaccine formulations incorporating bacterial capsules have been developed against a number of pathogens. In general, capsule vaccines are immunogenic in humans and non-toxic (Jennings, Curren. Top. Microbiol. Immunol., 150: 97-127 (1990)). One of the general problems associated with capsule vaccines is the poor immunogenicity of all polysaccharides in infants, and the fact that many of the capsular vaccines are directed at diseases that are particular threatening to the pediatric population. Based on murine studies, pure polysaccha- 105-111 (1983)); and type 6A *Streptococcus pneumoniae* (Chu et al., Infect. Immun. 40: 245-256 (1983)) have all improved following conjugation to proteins.

*C. jejuni* capsule, as defined in this application, is a generic term for capsular polymers, which are composed of repeating polysaccharide structures. The repeating structures can be homopolymers, defined as a repeating single sugar moiety, or repeating oligosaccharides (i.e. disaccharides or trisaccharides, etc.). A number of species of capsular repeating polysaccharide polymers have been identified. To illustrate the genus of capsular polysaccharide structures, Table 2 lists known capsular polysaccharide structures for *Campylobacter* strains.

TABLE 2

| Strain/HS type | Structure | Reference |
|---|---|---|
| HS3 | →4-α-D-Gal-(1→3)(3-hydroxypropanoyl)-L-glyero-α-D-ido-Hep-(1→ | Aspinall, et al (1995 |
| HS19 | →4)-β-D-GlcA-(1→)-β-D-GlcNAc-(1→<br>(GlcA units are present as amides of 2-amino-2-deoxyglycerol) | Aspinall, et al., 1994 (a and b) |
| HS23/36 | Four closely-related polysaccharides:<br>→3)-β-D-GlcNAc-(1→3)-α-D-Gal-(1→2)-6d-α-D-altro-Hep-(1→;<br>→3)-β-D-GlcNAc-(1→3)-α-D-Gal-(1→2)-6d-3-O-Me-α-D-altro-Hep-(1→;<br>→3)-β-D-GlcNAc-(1→3)-α-D-Gal-(1→2)-D-glycero-α-D-altro-Hep-(1→;<br>→3)-β-D-GlcNAc-(1→3)-α-D-Gal-(1→2)-3-O-Me-D-glycero-α-D-altro-Hep(1→ | Aspinall, et al., 1992 |

TABLE 2-continued

| Strain/HS type | Structure | Reference |
|---|---|---|
| 81116 | Two polysaccharides at a ratio of 3A:1B, where<br><br>$\quad\quad\quad\quad$ OAc (30%) $\quad\quad\quad\quad$ OAc (20%)<br>$\quad\quad\quad\quad\quad\quad\downarrow\quad\quad\quad\quad\quad\quad\quad\downarrow$<br>$\quad\quad\quad\quad\quad\quad$ 3 $\quad\quad\quad\quad\quad\quad\quad$ 6<br>A = →3)-β-D-Glc-(1→2)-α-D-GlcA-(1→3)-α-D-Man-(1→3)-α-D-Glc-(1→<br>B = →3)-β-D-GlcNAc-(1→6)-α-D-Glc-(1→4)-α-D-Gal-(1→<br>$\quad\quad\quad\quad\quad\quad\quad\quad\quad\quad\quad\quad\quad\quad\quad\quad\quad\quad\quad\quad$ 3<br>$\quad\quad\quad\quad\quad\quad\quad\quad\quad\quad\quad\quad\quad\quad\quad\quad\quad\quad\quad\quad$ ↑<br>$\quad\quad\quad\quad\quad\quad\quad\quad\quad\quad\quad\quad$ β-D-GlcNAc-(1 | Muldoon, et al., 2002 |
| NCTC 11168(HS2) | $\quad\quad$ 6-O-Me-D-L-α-L-glc-Hepp-(1<br>$\quad\quad\quad\quad\quad\quad\quad\quad\quad\quad\quad$ ↓<br>→2-β-D-Ribf-(1→5)-β-D-GalfNAc-(1→4)-α-D-GlcpA6(Ngro)-(1→<br>(Glucuronic acid is amidated with 2-amino-2-deoxyglycerol at C-6) | St. Michael, et al., 2002 |
| HS41 | Two closely related polysaccharides:<br>→2)-β-L-Araf-(1→2)-β-D-6d-altro-Hepf-(1→2)-β-L-6d-altrof-(1→(75%; and<br>→2)-β-L-Araf-(1→2)-β-D-6d-altro-Hepf-(1→2)-α-D-Fucf-(1→(25%) | Hannify, et al., 1999 |
| HS30 (C. coli) | $\quad\quad\quad\quad$ →5-Ribitol-1-P→<br>$\quad\quad\quad\quad\quad\quad\quad$ 2<br>$\quad\quad\quad\quad\quad\quad\quad$ ↑<br>6d-β-D-talo-Hep-(1→4)-β-D-GlcNAc-(1 | Aspinall, et al., 1993 |
| HS1 | →4)-β-D-Gal-(1→2)-(R)-Gro-(1-P→<br>(with two branches at C-2 and C-3 of Gal of β-D fructofuranoses that are further substituted at C-3 with O-methyl phosphoramidate groups | Aspinall 1998; McNally, et al., 2005 |
| HS 4, 13, 64 (GC8486) | →3)-6-d-β-D-ido-Hep-(1→4)-β-D-GlcNAc-(1→<br>With O-methyl phosphoramidate units present in non-stoichiometric amounts at the O-2 and/or O-7 positions of 6-deoxy-beta-D-ido-Heptose. | Chen, et al. 2008 |
| 81-176 (HS23/36) | →)3-α-D-Gal-(1→2)-6d-3-O—Me-α-D-altro-Hep-(1→3)-β-D-GlcNAc-(1→<br>$\quad\quad\quad\quad\quad\quad\quad\quad\quad\quad$ 2<br>$\quad\quad\quad\quad\quad\quad\quad\quad$ [MeOP(O)N]$^\pm$ | Kanipes, et al., 2006 |

SUMMARY OF INVENTION

An object of this invention is an anti-*C. jejuni* immunogenic composition, composed of a capsule polysaccharide polymer. The polymers are useful as components of immunogenic compositions without the likelihood of inducing GBS.

Another object of the invention is an isolated *C. jejuni* capsule carbohydrate polymer that is conjugated to a carrier protein. Yet, another object of the invention is a method of administering the carrier conjugated or unconjugated anti-*C. jejuni* capsule polysaccharide composition in order to induce an immune response. A still further object of the invention is a method of forming a carbohydrate conjugation to a protein carrier via a heptose or arabinose monosaccharide.

FIG. 1. Composition analysis of *C. jejuni* strain ATCC No. 43442 (HS:15).

Figure 2:
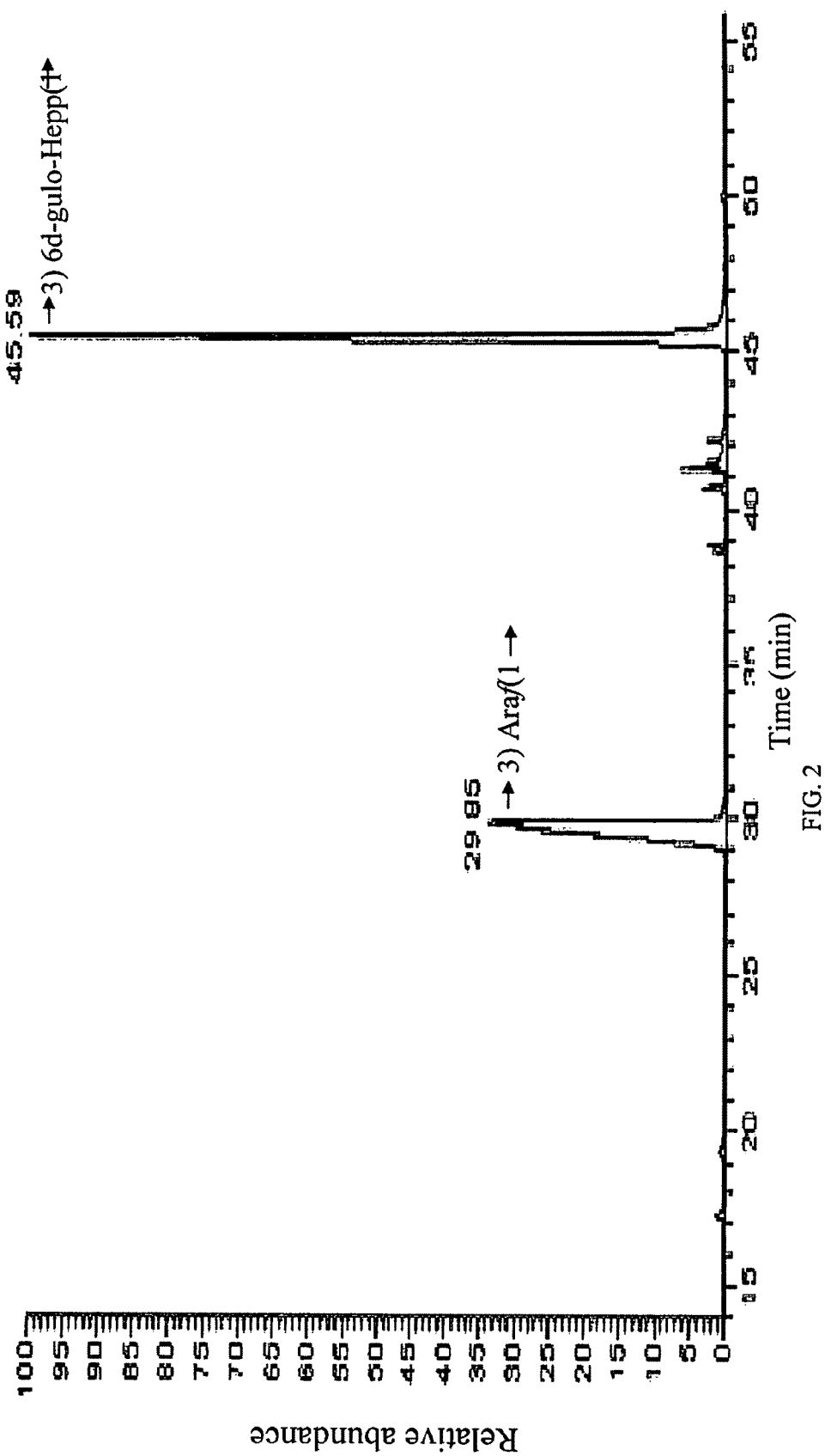

FIG. 2. Linkage analysis on capsule polysaccharide of *C. jejuni* ATCC No. 43442 (HS: 15).

Figure 3:
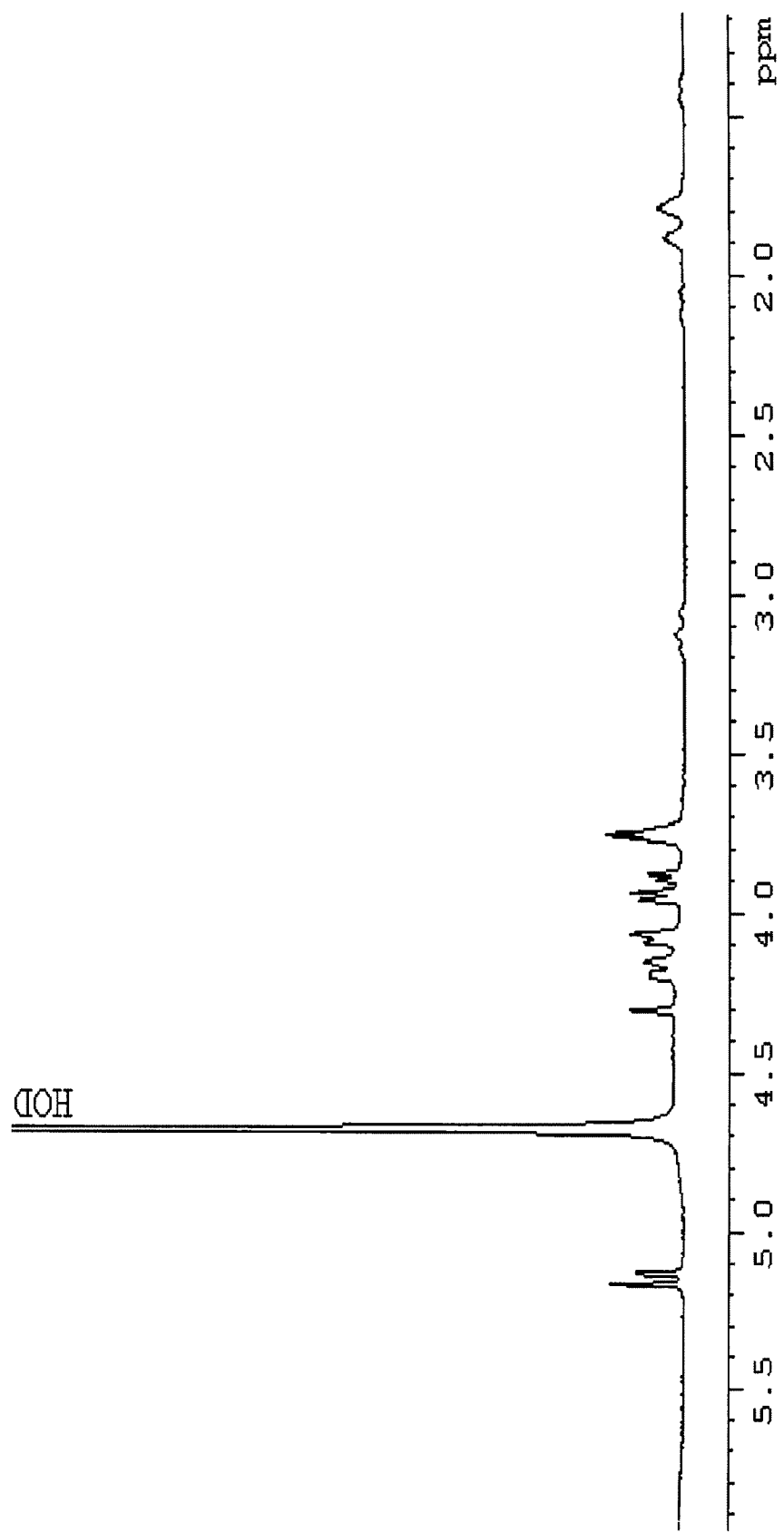

FIG. 3. One-dimensional $^1$H-NMR spectrum of the CPS of *C. jejuni* ATCC No. 43442.

Figure 4:
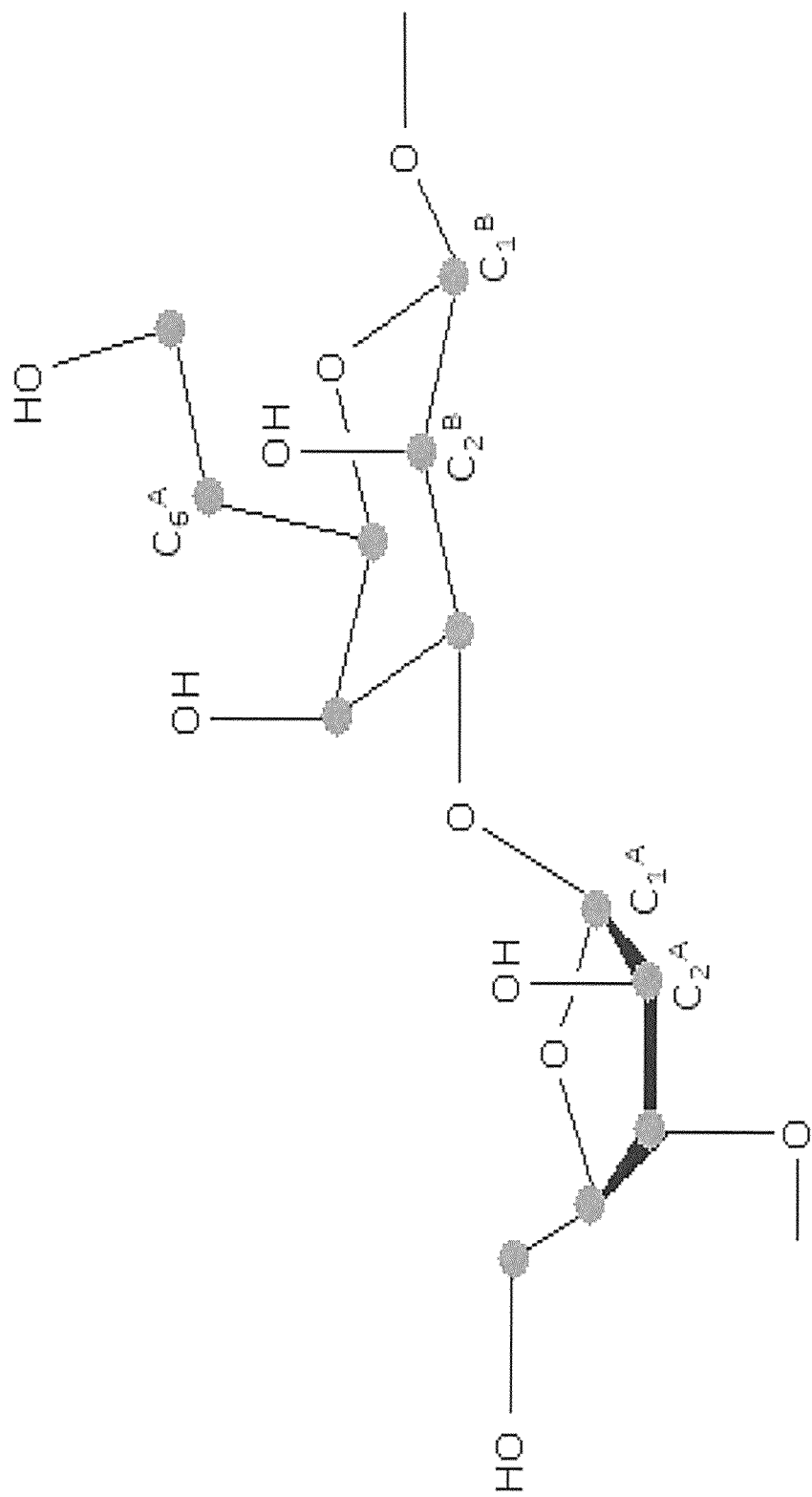

FIG. 4. Five and seven-carbon sugar identified by $^1$H/$^{13}$C HSQC of CPS of *C. jejuni* ATCC No. 43442.

Figure 5:
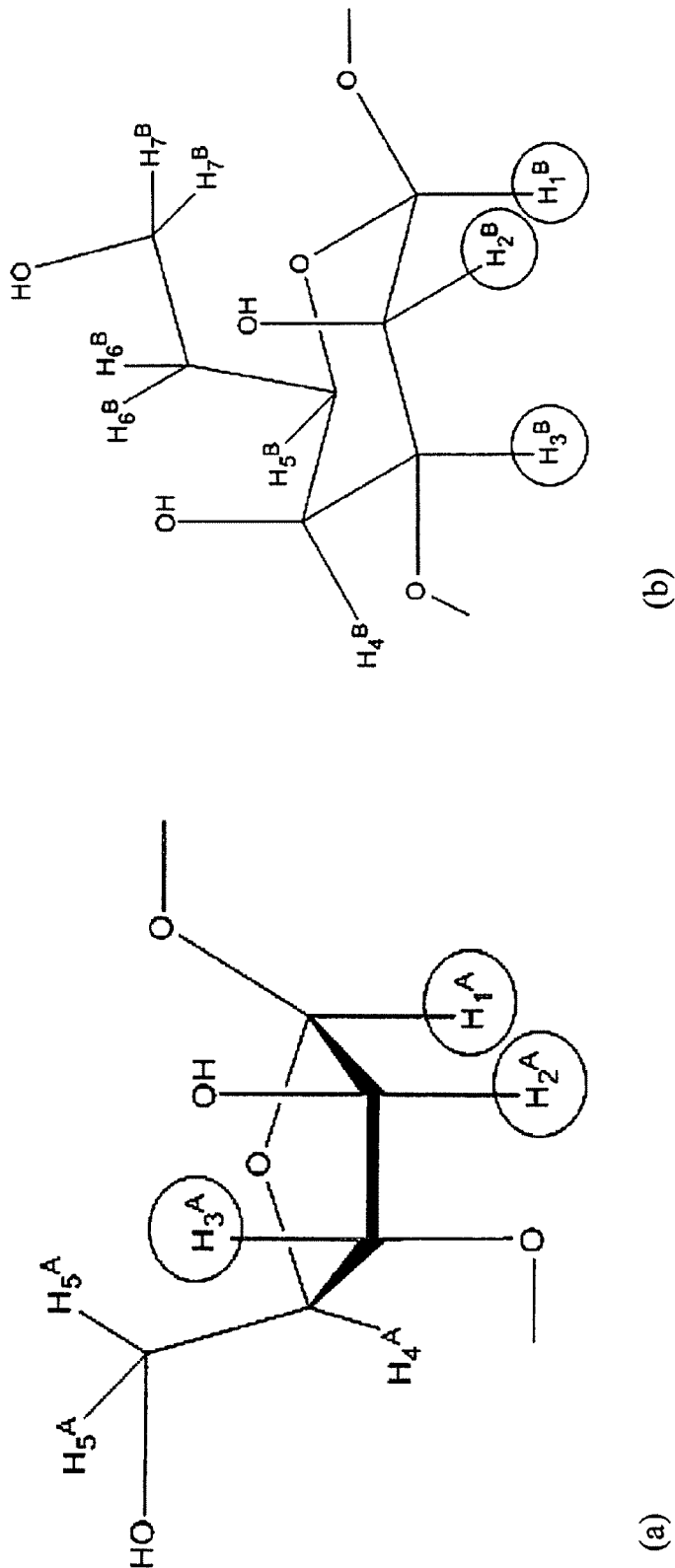

FIG. 5. Assignment of protons rendering cross-peaks within α-Araf (a) and 6d-gulo-Hepp (b) from COrrelated SpectroscopY ($^1$H/$^1$H COSY) of CPS of *C. jejuni* ATCC No. 43442.

Figure 6:
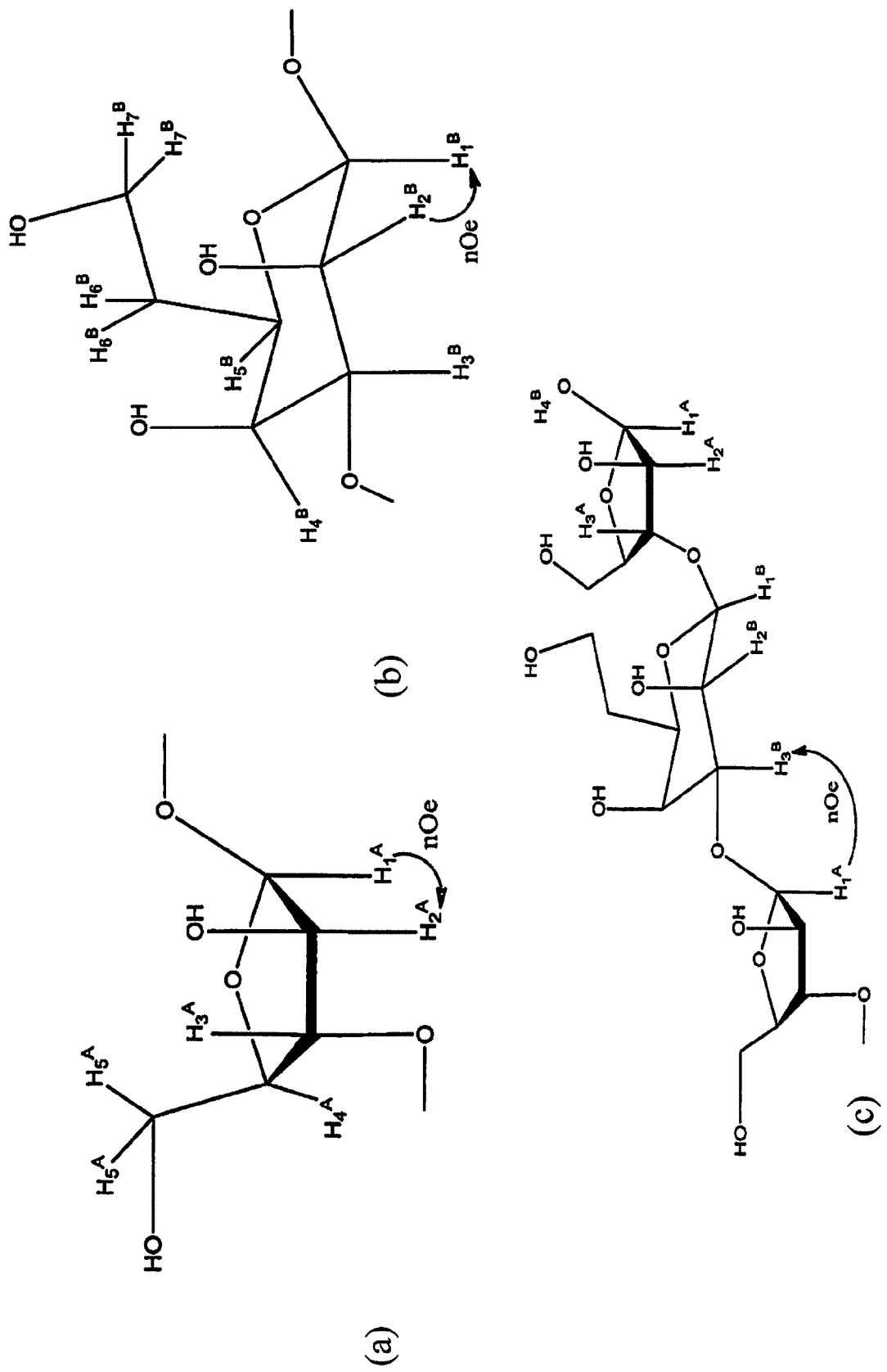

FIG. 6. Interaction of protons in the chemical linkages from 2D $^1$H/$^1$H NOESY of CPS of *C. jejuni* ATCC No. 43442. Shown are the inter-nOe interactions of (a) α-Araf; (b) α-6d-gulo-Hepp; and (c) [→3)-α-Araf(1→3)-α-6d-gulo-Hepp(1→] linkages.

Figure 7:
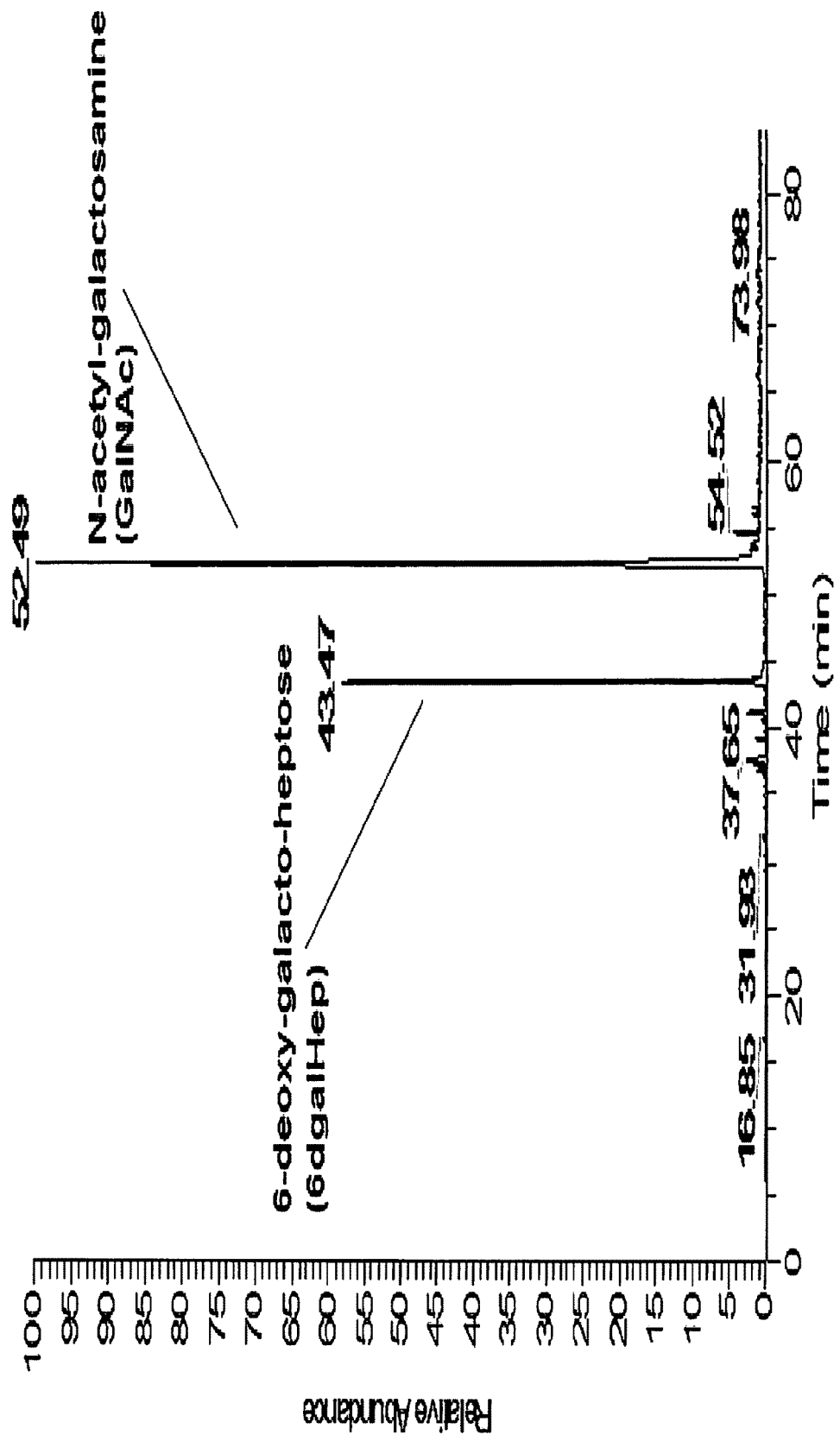

FIG. 7. Monosaccharide composition analysis on CPS of *C. jejuni* strain (ATCC no. 43438)(HS:10).

Figure 8:
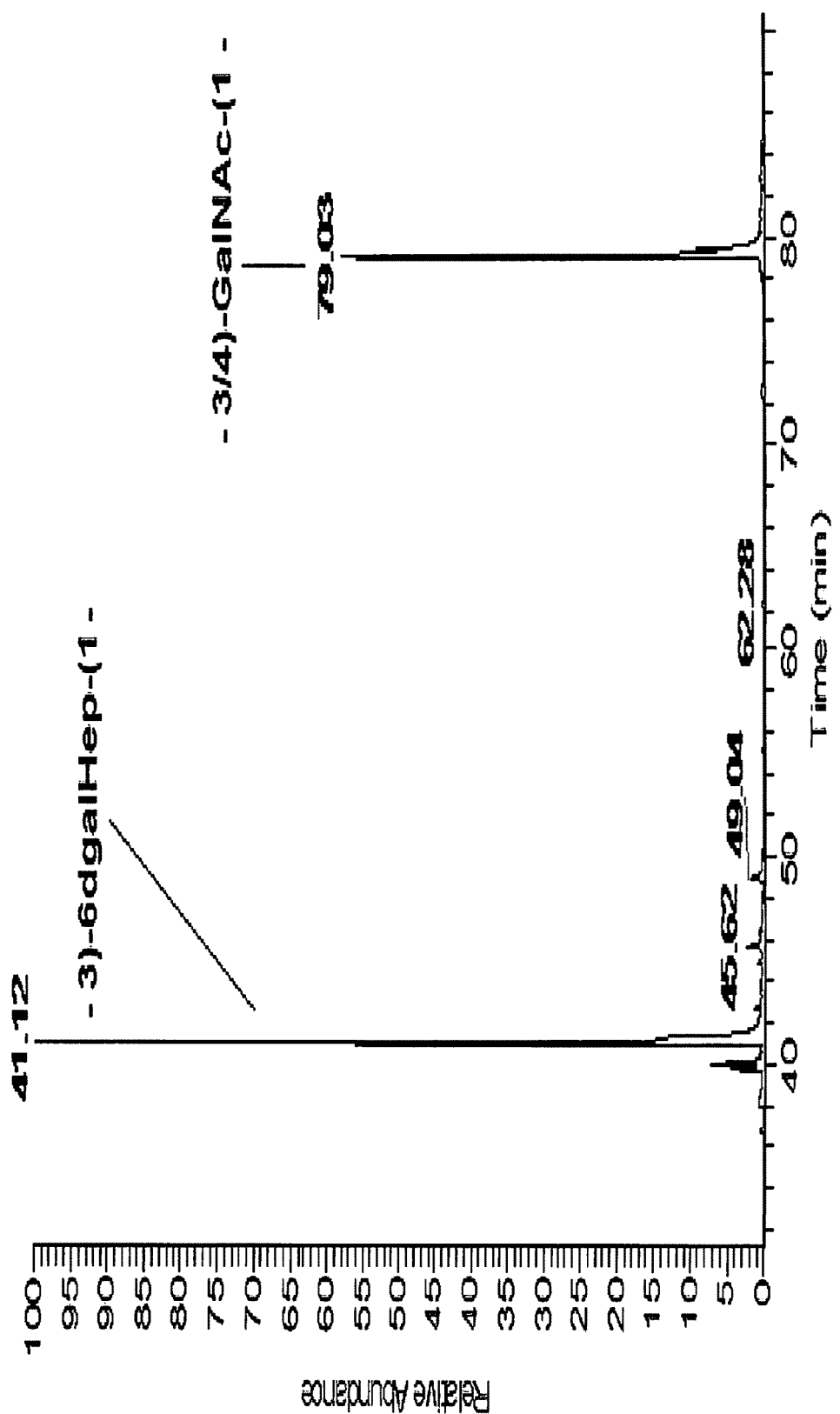

FIG. 8. Sugar linkage analysis of CPS of *C. jejuni* strain ATCC no. 43438.

Figure 9:
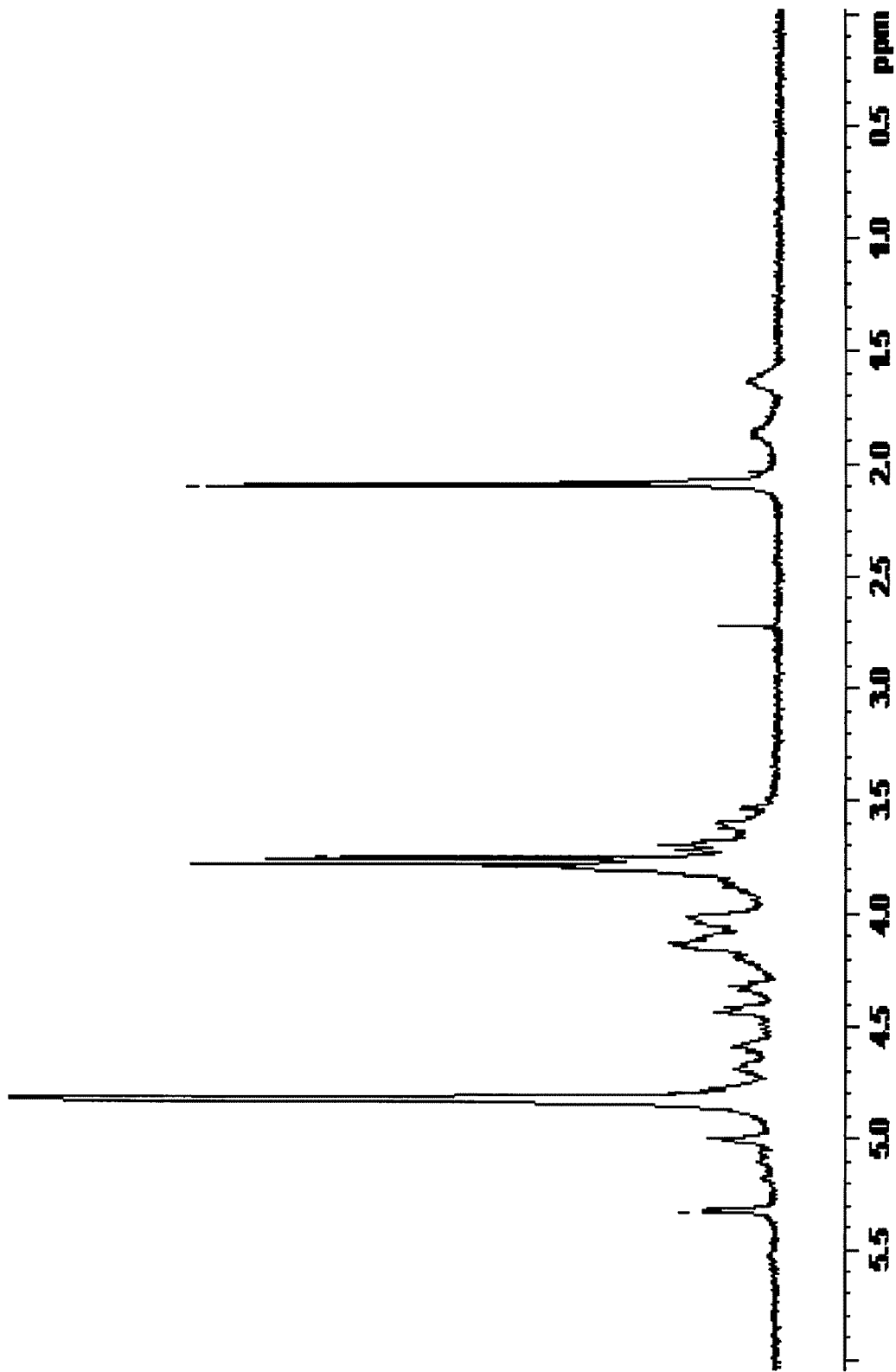

FIG. 9. $^1$H NMR spectrum of *C. jejuni* (ATCC no. 43438).

Figure 10:
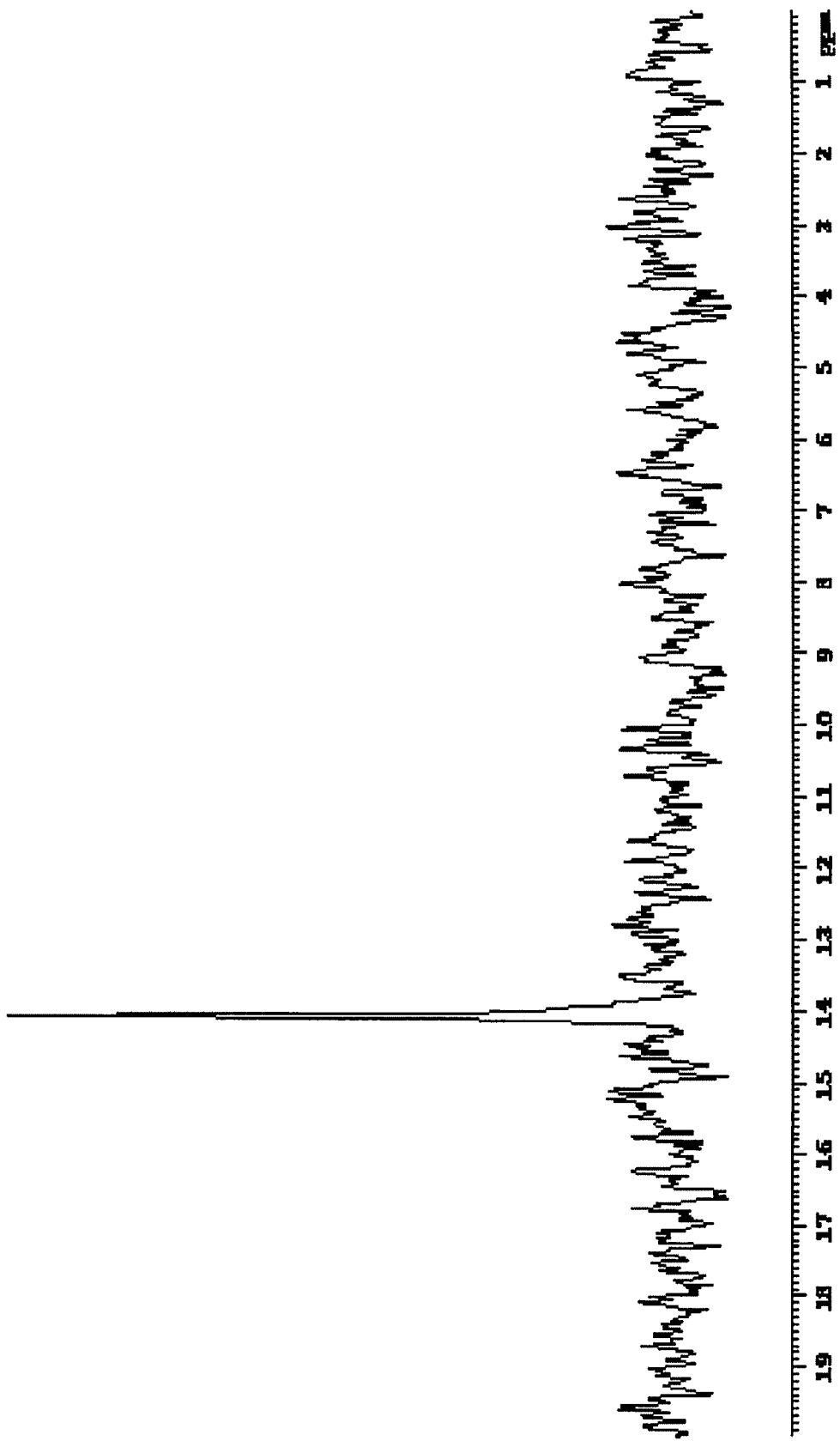

FIG. 10. $^{31}$P NMR spectrum of CPS of *C. jejuni* ATCC No. 43438.

Figure 11:
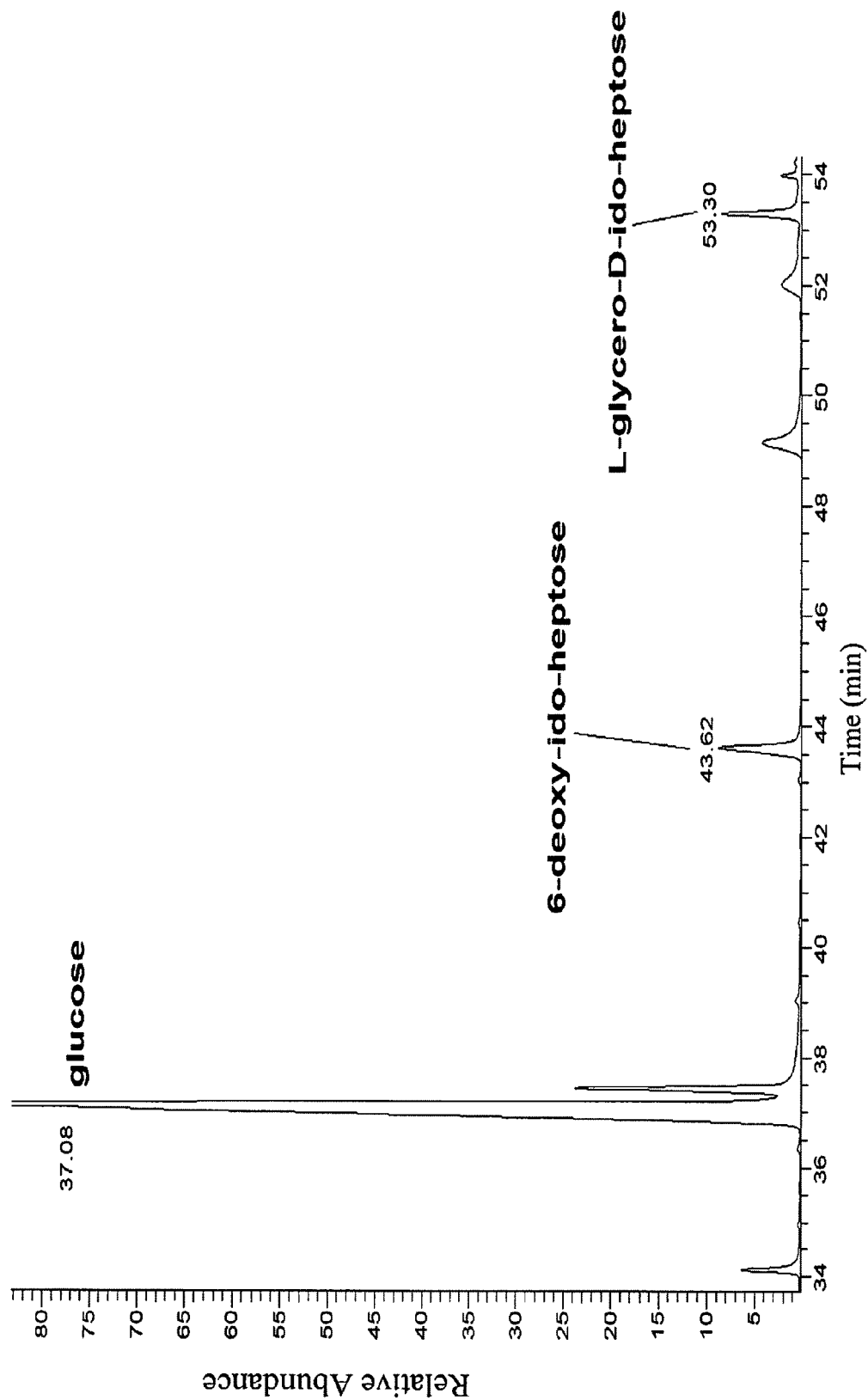

FIG. 11. Monosaccharide composition analysis on CPS of *C. jejuni* serotype (HS:13).

Figure 12:
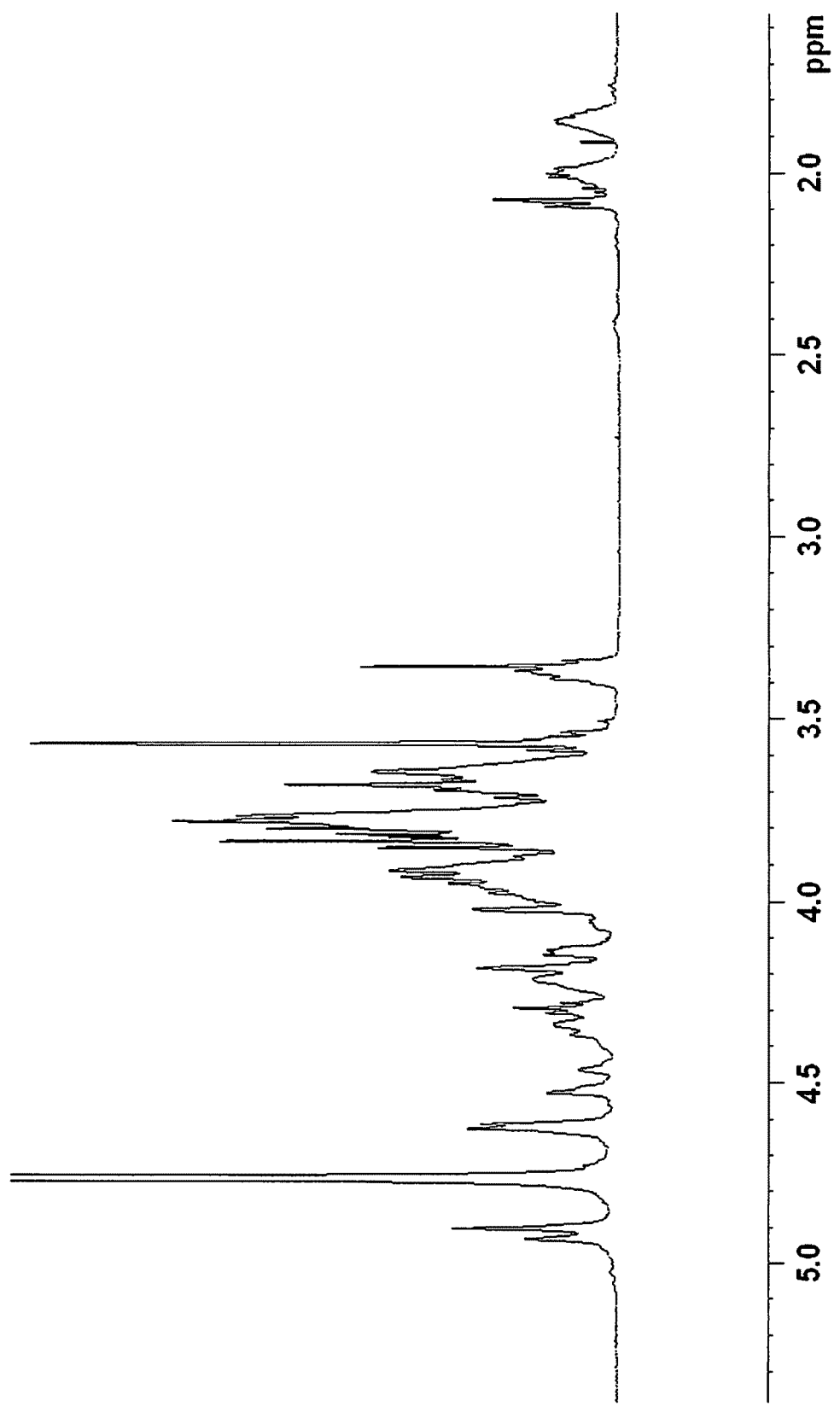

FIG. 12. $^1$H NMR spectrum of CPS of *C. jejuni* serotype HS:13.

Figure 13:
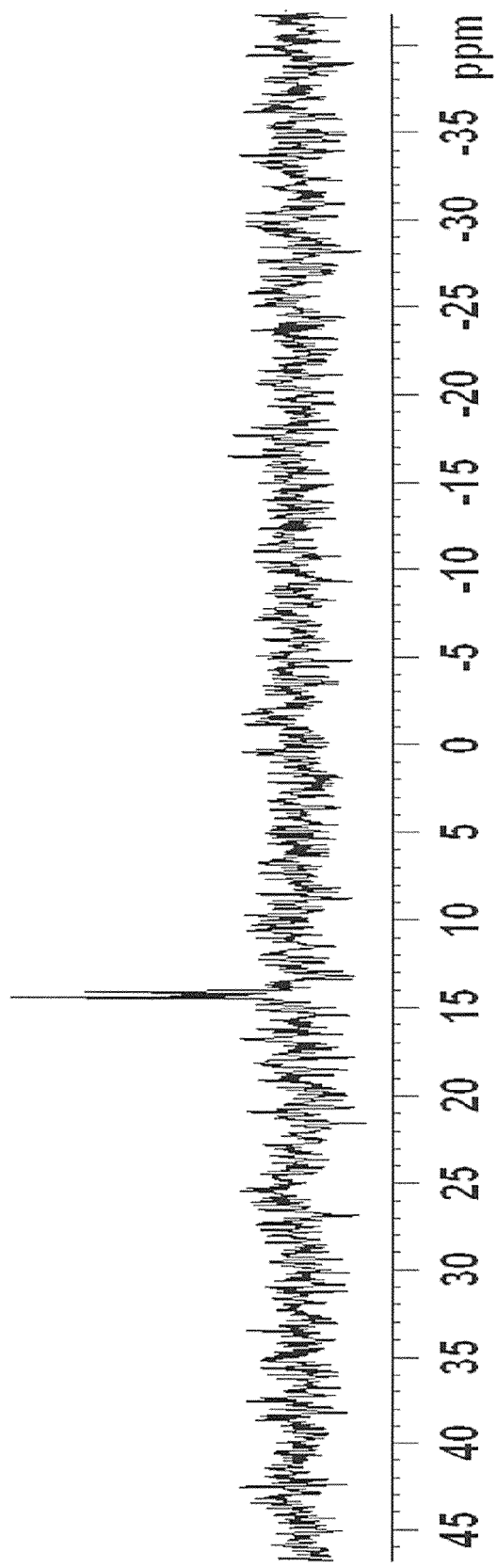

FIG. 13. $^{31}$P NMR spectrum of CPS illustrating two resonances for methyl-phosphoramidate units (MeOPN).

Figure 14:
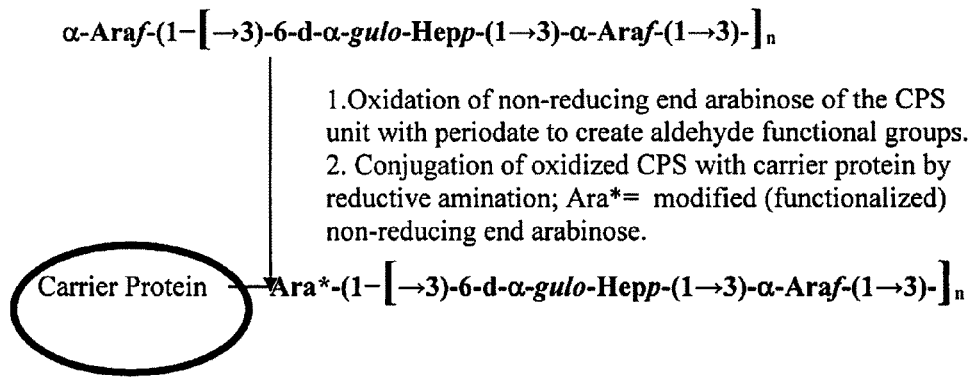
Figure 14:
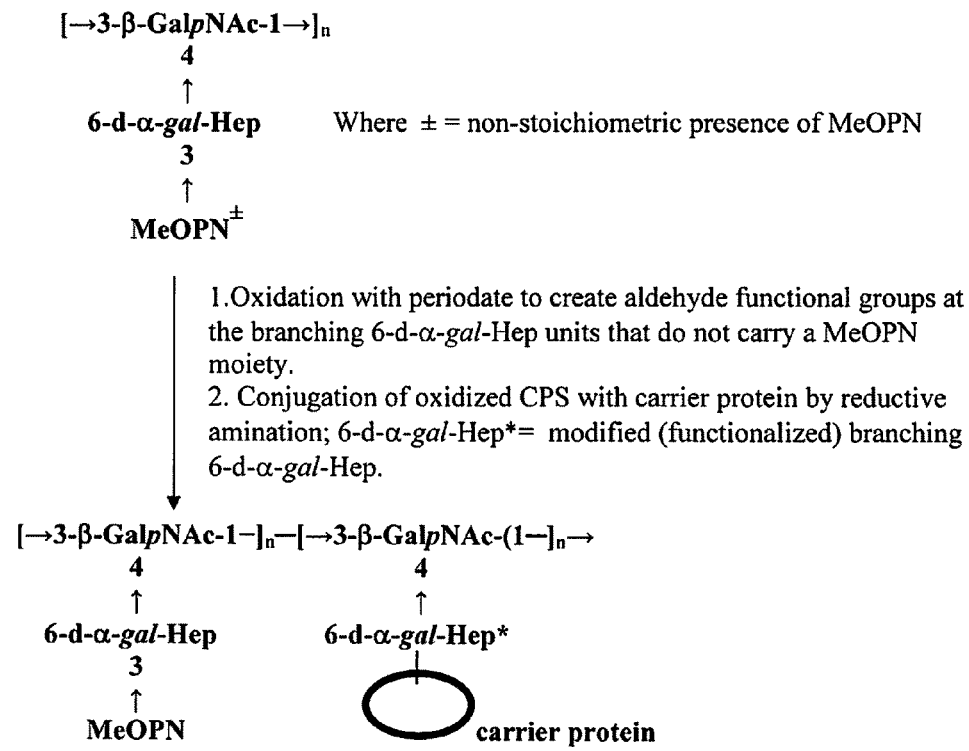

FIG. 14. Conjugation scheme for CPS carbohydrates. A) conjugation scheme of HS:15 via arabinose; B) conjugation scheme of HS:10 via heptose.

DETAILED DESCRIPTION OF PREFERRED EMBODIMENTS

*C. jejuni* capsular moieties are important in sero-determination. However, despite over 60 Penner serotypes having been identified, most *Campylobacter* diarrheal disease is caused by *C. jejuni* from a limited number of serotypes. Because of the importance of capsule structure in sero-determination, it is postulated that they are highly immunogenic structures. Additionally, they are also unlikely to exhibit the unwanted autoimmune induction caused by immuno-mimicry observed by lipooligosaccharides. Therefore, capsules or capsular components would be highly useful in anti-*C. jejuni* vaccines. *C. jejuni* capsules are composed of repeating polysaccharide structures. The repeating capsule polysaccharide (CPS) structures can be homopolymers, defined as a repeating single sugar moiety, or a repeating oligosaccharide, with or without branching sugars.

Generation and Extraction of the Capsular Polysaccharide

*Campylobacter jejuni* cells were grown in porcine Brain-Heart Infusion (BHI) broth and sonicated to inactivate the cells. The CPS was extracted by hot water/phenol method previously employed for the same organism (Chen, et al., Carbohyd. Res. 243: 1034 (2008)). Cells were immersed in a water/phenol mixture (3:2 ratio by volume), which was heated to 70° C. with stirring for 6 hours. The suspension was cooled and separation of the mixture into two separate layers (the aqueous layer and the phenol layer) and extraction of the aqueous layer was performed. Rotary evaporation was employed to concentrate the extracted aqueous layer. The resulting concentrate was placed on dialysis and subjected to ultracentrifugation to isolate the CPS (soluble) from the LOS (insoluble) (Chen, et al., Carbohyd. Res. 243: 1034 (2008)). The supernatant in this separation, containing the desired CPS, was frozen and lyophilized for future use.

Analysis of Monosaccharide Composition

Monosaccharide composition analysis was performed by derivatization of the CPS sample using the alditol acetate method (Chen, et al., Carbohyd. Res. 243: 1034 (2008); Fox, et al., *Analysis of Carbohydrates by GLC and MS*, CRC Press, Inc, Boca Raton, pp. 87-118 (1989)) on a sample of the CPS. The sample was treated with 4 M trifluoroacetic acid (TFA) at 105° C. with stirring to effect hydrolysis of glycosidic bonds. Subsequently, reduction of the aldose form of the monosaccharides present was achieved by sodium borodeuteride ($NaBD_4$) reduction with stirring overnight at room temperature to render the alditol form. Acetylation of the alditol monosaccharides resulting from the previous step was achieved by immersing the sample in acetic anhydride at 105° C. for 1.5 hrs with stirring. Following the removal of impurities by dichloromethane extraction, the resulting alditol acetate-derivatized sugars were applied to a GC/MS for separation and fragmentation. Analysis by GC/MS was performed using a ThermoFinigan PolarisQ spectrometer in electron impact (EI) mode.

Analysis of the CPS Monosaccharide Linkages

Linkage analysis of the monosaccharide units established from composition analysis was performed by the partially-methylated alditol acetate (PMAA) procedure (Chen, et al., Carbohyd. Res. 243: 1034 (2008); Carpita and Shea, *Analysis of Carbohydrates by GLC and MS*, CRC Press, Inc, Boca Raton, pp. 157-216 (1989)). In this method, the CPS sample is suspended in DMSO. This operation was performed overnight with constant stirring to ensure that the suspension was complete. Powdered sodium hydroxide (NaOH) was then added to the reaction vial for the establishment of basic reaction conditions and, shortly after, iodomethane was added to effect functional group inter-conversion from alcohol to ether on all non-bonded positions of the polysaccharide. The resulting methylated polysaccharide was extracted with dichloromethane prior to drying by application of trace heat. The methylated polysaccharide derivative was then processed by the alditol acetate procedure briefly outlined above.

Nuclear Magnetic Resonance Spectroscopy

A sample of the CPS result rendered from the water/phenol extraction and ultracentrifugation was exchanged in deuterium oxide ($D_2O$). This was achieved through suspension of the sample in $D_2O$ followed by freezing and lyophilizing. The process was repeated twice. The generated NMR sample was analyzed by a Bruker BioSpin ULTRASHIELD™ (Bruker Biospin Ltd, Ontario, Canada) 600 MHz nuclear magnetic spectrometer and a Bruker AMX™ (Bruker, Biospin, Ltd, Ontario, Canada) 400 nuclear magnetic spectrometer at room temperature. Before NMR experiments were conducted on the prepared sample, a reference containing trimethylsilane (TMS; $\delta_H$ 0.00) was run to aid in identification of the HOD signal (used as an internal reference). Resulting data was analyzed with Bruker BioSpin's TOP SPIN™ 2.1 software package.

Example 1

Isolation and Analysis of *Campylobacter jejuni* Capsule Structures

*Campylobacter jejuni* Strain HS: 15

Monosaccharide Composition and Linkage Analysis of the *Campylobacter jejuni* HS:15 CPS by GC/MS Composition analysis of the CPS of *C. jejuni* strain ATCC No. 43442 (HS: 15) revealed the presence of arabinose (Ara) and a 6-deoxy-heptose (6d-Hep) (FIG. 1). Fragmentation analysis of the Arabinose peak revealed characteristic peaks at 217/218 and 289/290 (m/z). Following fragmentation of the 6d-Hep peak, characteristic peaks were located at 159, 303 and 375 (m/z). The identity of the 6d-Hep was probed by comparison to the alditol acetate derivatives of synthetic 6-deoxy-heptoses and was determined to be 6-deoxy-gulo-heptopyranose. Through a linkage analysis performed on the CPS of *C. jejuni* ATCC No. 43442 (HS: 15), it was concluded that the Ara monosaccharide was present in the oligosaccharide repeat as a 3-substituted unit [→3)-Ara-(1→] and that the 6d-gulo-Hep was present also as a 3-linked unit [→3)-6d-gulo-Hep(1→] (FIG. 2). Small amounts of terminal Ara [Ara-(1→] were also observed, which pointed to the fact that the CPS was terminated at the non-reducing end by an Ara residue. The Ara unit was found to be present in the furanose form (Araf) while the 6d-gulo-Hep (as aforementioned) was found to be in the pyranose form (6d-gulo-Hepp).

NMR Spectroscopic Analysis of the *Campylobacter jejuni* HS:15 CPS

The one-dimensional (ID) $^1$H-NMR spectrum of the CPS of *C. jejuni* strain number ATCC No. 43442 rendered two anomeric resonances at δ 5.168 (residue A) and δ 5.132 (residue B) (FIG. 3). Two up-field peaks occurring at δ 1.792 and δ 1.884 were attributable to the methylene protons of the 6d-gulo-Hepp. A two-dimensional (2D) $^1$H/$^{13}$C HSQC revealed the presence of 12 unique carbons (FIG. 4). By comparison to the previously mentioned reporter peaks in the 1D $^1$H-NMR spectrum, the anomeric carbons of residue A (δ 109.39) and residue B (δ 95.59) were identified.

Also present was the deoxy-carbon of the 6d-gulo-Hepp at δ 31.56. Employing the key peaks from the 1D $^1$H-NMR spectrum, a $^1$H/$^1$H COSY was employed for assignment of ring protons in the oligosaccharide repeat (FIG. 5). Residue A was determined to correspond to the Araf unit present (H-2 at δ 4.311; H3 at δ 4.091). Residue B was determined to be the 6d-gulo-Hepp (H-2 at δ 4.063; H-3 at δ 3.959; H-5 at δ 4.202; H-6,6' at δ 1.778 and δ 1.890; H-7 at δ 3.751). A 2D $^1$H/$^1$H NOESY experiment was also conducting using the CPS of *C. jejuni* PG2887 (from ATCC No. 43442) for confirmation of sugar units, demonstrating a strong relationship between internal protons of isolated sugar units (Araf H-1 at δ 5.143 to H-2 at δ 4.304; 6d-gulo-Hepp H-1 at δ 5.137 to H-2 at δ 4.062) (FIG. 6). Further evidence to support the linkage determined by chemical means was shown in the strong correlation between H-1 of residue A (Araf) (δ 5.154) and H-3 of residue B (6d-gulo-Hepp) (δ 3.951) for a [→3)Araf(1→3)6d-gulo-Hepp(1→] linkage. The interaction between H-1 of residue B (the 6d-gulo-Hepp unit) at δ 5.147 and H-3 of residue A (the Araf unit) at δ 4.148 was found to be significantly weaker for a [→3)6d-gulo-Hepp(1→3)Araf(1→] linkage.

Compositional analysis of the extracted capsular polysaccharide revealed the presence of the arabinose and a 6-deoxy-heptose. Arabinose, a five carbon sugar, has been described previously in *C. jejuni* CPS constructs (Karlyshev, et al., Molec. Microbiol, 55: 90 (2005); Hanniffy, et al., Carbohydr. Res., 319: 124 (1999)).

Fragmentation analysis by mass spectrometry resulted in characteristic peaks at 289/290 and 217/218 (mix) as shown in FIG. 1(a). Of these, the peak occurring at 290 (m/z) was determined to be most informative as it corresponded to the full derivatized linear chain less the last (C-5) carbon. The peak occurring at 218 (m/z) is also significant as it negates the possible presence of arabinitol (the straight chain version of arabinose, lacking aldehyde functionality at C-1). In the later case, only odd numbered peaks would have been observed as the borodeuteride reduction would not have an aldehyde substrate on which to operate and the deuterium (the reason that even peaks arise) would not have been incorporated. 6d-Heptoses in unusual configurations (such as altro and ido configurations) is a characteristic trend for the CPS of *C. jejuni* (Monteiro, et al., Infect. Immun., 77: 1128 (2009); Chen, et al., Carbohyd. Res., 343: 1034 (2008)).

Fragmentation analysis by mass spectrometry resulted in characteristic peaks at 159, 303 and 375 (m/z) (FIG. 1(b)). The peaks detected at 375 and 303 (m/z) are significant as they are suggestive of the 6-deoxy-carbon present in the C-6 position. However, it is the peak occurring at m/z=159 that is particularly important. This peak arises from the cleavage of the sugar backbone from the bottom of the chain following C-5 (FIG. 1(b)) and is the first possible cleavage following the 6-deoxy carbon on the backbone. If the heptose contained hydroxyl functionality at C6, one would expect to see a peak at 145 (m/z). However, this peak was not observed.

The identity of the 6d-Hep monosacharide unit was determined to be 6d-gulo-heptose (6d-gulo-Hep) by comparison to synthetic sugar derivatives. The original synthetic sugars used to generate the synthetic spectra were prepared as described by Pakulski and Zamojski (Tetrahedron 51: 871 (1995) and used to generate the derivate for comparison. Through the careful comparison of characteristic peaks in each rendered spectrum for the synthetic sugars, the identity of the 6d-Hep found in the CPS of *C. jejuni* PG2887 (ATCC No. 43442) (HS:15) was concluded to be 6d-gulo-Hep.

Following identification of the monosaccharide units present, PMAA analysis determined that both the Ara and the 6d-gulo-Hep unit were 3-linked. PMAA analysis was profoundly valuable as cleavage of the sugar back bone is preferred following methyl ether presence rather than at acetylated carbons due to enhanced stabilization of the positive charge generated by mass spectrometry in electron impact (EI) mode (Carpita and Shea, *Analysis of Carbohydrates by GLC and MS*, CRC Press, Inc., Boca Raton, pp. 157-216 (1989)). With regards to the 3-linked Ara unit, key peaks were notably present at 118 and 233 (m/z) (FIG. 2(a)). These peaks indicate the substitution of methyl ether at the C2 position in the linearized monosaccharide. Furthermore, it can be determined that a linkage at this position was not present as only free hydroxyl groups are converted to O-methyl ethers in the primary derivatization step of the PMAA procedure (Carpita and Shea, *Analysis of Carbohydrates by GLC and MS*, CRC Press, Inc., Boca Raton, pp. 157-216 (1989)).

As important as characteristic peaks are to these spectra, peaks that are not revealed by analysis are also uniquely informative. Confirmation of the 3-linked status of the Arabinose unit, for example, was confirmed by the absence of a peak at 162 (m/z); this peak would be observed in terminal arabinose [i.e. Ara(1→], resulting from O-methyl present at C3 rather than O-acetyl. Based on fragmentation analysis, it was also concluded that the 3-linked Ara unit was present in the furanose form. This was determined by the significant presence of a peak at 233 (m/z) with a very minor peak at 234 (m/z). Had the Ara unit been present in the pyranose form, it is likely that the peak at m/z=234 (arising from cleavage following O-methyl substitution at C4 in place of O-acetyl) would be more pronounced.

Analysis of the 6d-gulo-Hep unit was performed in the same fashion, with characteristic peaks found at 234 and 175 (m/z). These peaks are indicative of the presence of methyl ether functionality at C4 of the straight-chain monosaccharide (rendered from subsequent derivatization) and, therefore, no linkage at this position. Additionally, a lack of a peak at 162 (m/z) was used to deduce the 3-linked nature of the 6d-gulo-Hep as it was in the case of the previous monosaccharide unit. By linkage analysis, it was also determined that the 6d-gulo-Hep was in the pyranose form. This is in keeping with the literature as investigations into the conformations of 6d sugars determined that 6d-gulo-Hep was more likely to be found in the pyranose form than the furanose form (Shashkov, et al., Carbohyd. Res. 330: 289 (2001)). Were this unit in the furanose form, one would not see either of the previously mentioned peaks due to substitution of O-acetyl at the C4 position.

1D $^1$H-NMR of the CPS performed in $D_2O$ revealed two peaks downfield at δ 5.168 (residue A) and δ 5.132 (residue B) (FIG. 3(a)). In the proton NMR spectrum, it has been determined that this region is used as a reporter region for the anomeric proton resonances of saccharides (Agrawal, P. K., Phytochemistry 31: 3307 (1992)). Two peaks were detected in this region, a finding that is consistent with both composition and linkage analyses previously discussed. This general region of anomeric resonances can further be divided into two different regions: α-sugars, whose anomeric resonances appear between δ 4.8-5.3; and β-sugars, whose anomeric resonances are found between δ 4.4-4.8 (Agrawal, P. K., Phytochemistry 31: 3307 (1992)). Due to the location of the anomeric resonances found experimentally, it was concluded that both monosaccharide units in the oligosaccharide repeat were in the α-configuration.

The 1D $^1$H-NMR is also capable of rendering evidence of 6-deoxy sugars in the upfield region of the spectrum; a region typically associated with alkane protons (Monteiro, et al., Infect. Immun. 77: 1128 (2009); Carpita and Shea, *Analysis of Carbohydrates by GLC and MS*, CRC Press, Inc., Boca Raton, 157-216 (1989): Agrawal, P. K., Phytochemistry 31: 3307 (1992); Wade. L. G., *Organic Chemistry*, 4$^{th}$ ed., Prentice Hall, Upper Sadie River, N.J. (1999): Solomons and Fryhle, *Organic Chemistry*, 8$^{th}$ ed., Wiley, Inc. Hoboken, N.J. (2004)). In the experimental spectrum, it was found that two peaks were rendered in the upfield region at δ 1.792 and δ

1.884, further confirming the presence of the 6d-Hep unit. While alkane protons located in a standard hydrocarbon are typically even further up-field (between δ 1.3-δ 1.4 (Solomans and Fryhle, *Organic Chemistry*, 8$^{th}$ ed., Wiley, Inc, Hoboken, N.J. (2004; Shashkov et al., Carbohyd. Res., 330: 289 (2001)), neighboring electron-withdrawing alcohol substitution in the monosaccharide ring environment elicit de-shielding effects. With this de-shielding in place, the methylene resonances are shifted downfield.

Spectroscopic investigations into the different 6-deoxy heptoses performed by Shashkov et al. found that H-1 of 6d-gulo-Hepp presented with a chemical shift of 5.13 (Shashkov, et al., Carbohyd. Res., 330: 289 (2001)). By comparison to this value, it was determined that the resonance of δ 5.132 previously referred to as residue B belonged to the 6d-gulo-Hepp monosaccharide unit. By elimination, then, it was concluded that the downfield resonance was attributable to the Araf unit of the oligosaccharide repeat.

Assignment of the other ring proton resonances could not be clearly assigned in the 1D $^1$H-NMR spectrum as the majority of remaining resonances arise between δ 3.0-4.2 (Agrawal, P. K., Phytochemistry, 31: 3307 (1992)). Resonances from H-2 to H-5 of the Araf and H-2 to H-5, H-7, and H-7' of the 6d-Hepp could not be concretely assigned, accordingly alternative spectroscopic methods were employed.

A 2D $^1$H/$^{13}$C HSQC revealed the presence of 12 unique carbons consistent with the proposed oligosaccharide composition of a 5-carbon and a 7-carbon sugar (FIG. 4). Cross-peaks found in this spectrum arise from each unique proton attached to carbon atoms in the saccharide ring (Jacobsen, NMR Spectroscopy Explained: Simplified Theory, Applications and Examples for Organic Chemistry and Structural Biology, Wiley-Interscience: Hoboken, N.J. (2007)). Although it would appear as though there are more than 12 unique peaks in this spectrum, it is important to note that both C-6 and C-7 of the 6d-gulo-Hepp unit will appear as doublets due to the attachment of two protons to these carbons.

This spectrum was also used for the assignment of ring carbons, giving a chemical shift of δ 109.39 to C-1 of α-Araf (residue A) and δ 95.59 to C-1 of α-6d-gulo-Hepp (residue B). Literature values for these resonances are δ 101.9 (for α-Araf) and δ 94.1 (for α-6d-gulo-Hepp) (Hanniffy, et al., Carbohydr. Res., 319: 124 (1999); Shashkov, et al., Carbohyd. Res., 330: 289 (2001)) for monosaccharide units. The experimental values derived from the analysis of the intact CPS of *C. jejuni* PG2887 (ATCC No. 43442) (HS:15) were notably downshifted from both of these results, however, both units are still part of the polysaccharide chain. It would appear then that, with the links intact, the chemical environment of the monosaccharide carbons is altered. Similar downfield shifting was observed in the analysis of a cell membrane-linked polysaccharide of *C. jejuni* 176.83, whereby a 2-linked Ara unit in the polysaccharide demonstrated a greater chemical shift than the monosaccharide unit (Hanniffy, et al., Carbohydr. Res., 319: 124 (1999)).

2D $^1$H/$^1$H COSY analysis of bio-molecules, like the capsular polysaccharide under consideration, is useful for the assignment of protons as it renders cross-peaks as long as the protons are within 2-3 bonds (Jacobsen, NMR Spectroscopy Explained: Simplified Theory, Applications and Examples for Organic Chemistry and Structural Biology, Wiley-Interscience: Hoboken, N.J. (2007)). Using this method, then, it is possible to connect neighboring protons by progressing stepwise through the rendered spectrum. As illustrated in FIG. 5, it was determined from the experimental spectrum that the chemical shifts of the protons attached to C-2 and C-3 of the α-Araf unit to be δ 4.311 and δ 4.091 respectively. As the end goal of ring proton assignment was so that the NOESY spectrum could be assessed for linkage, complete assignment is not reflected in FIG. 5.

For the 6d-gulo-Hepp unit, proton resonances for H-2 and H-3 were determined to be δ 4.063 and δ 3.959 respectively. Further investigation of the spectrum also revealed the presence of the methylene protons of the 6d-gulo-Hepp unit at δ 1.778 and δ 1.890. The presence of these peaks is in keeping with both the 1D $^1$H-NMR spectrum and chemical characterization methods previously discussed. Furthermore, the cross-peaks corresponding to H-5 and H-7 were assignable based on their spatial relationship with H-6,6' (δ 4.202 and δ 3.751, respectively). Of these, the proton resonance from H-7 is helpful as it serves to further prove the presence of the heptose saccharide.

With key proton resonances identified, a 2D $^1$H/$^1$H NOESY experiment was used to determine the interaction of protons in the linkages present. The results are illustrated by the structures given in FIG. 6. The 2D NOESY experiment is especially useful in this situation as it shows cross-peaks not only within the individual monosaccharide units but between them as long as the protons are within a distance of 5 Å of one another ((Agrawal, P. K., Phytochemistry, 31: 3307 (1992); Jacobsen, NMR Spectroscopy Explained: Simplified Theory, Applications and Examples for Organic Chemistry and Structural Biology, Wiley-Interscience: Hoboken, N.J. (2007); Mitchell and Costisella, *NMR—From Spectra to Structures*, Springer-Verlag, Berlin, Germany (2004)).

Beginning with the α-Araf unit, FIG. 6 (a), a strong intra-nOe relationship was found between H-1 (δ 5.143) to H-2 (δ 4.304). With regards to the chemical structure of the α-Araf unit, this interaction arises between two hydrogens that are located on the same side of the ring. Additionally, they are maintained within a distance of about 1.5 Å (from the carbon-carbon bond) for the interaction to occur (Lide, D. R., *CRC Handbook of Chemistry and Physics*, CRC Press, Boca Raton, Fla. (2003)). Similarly, the α-6d-gulo-Hepp unit (FIG. 6 (b)) demonstrated a similar intra-nOe interaction between H-1 (δ 5.137) and H-2 (δ 4.062).

Moving beyond the confines of the monosaccharide units, inter-nOe interactions were noted allowing for probing of the linkages present. The strongest inter-nOe interaction was found between H-1 of the (δ 5.154) and the H-3 of the α-6d-gulo-Hepp (δ 3.951) for a [43)-α-Araf(1→3)-α-6d-gulo-Hepp(1→] linkage FIG. 6 (c)). This is expected as linkage in this fashion would bring the hydrogens within the 5-Å limit of one another to permit cross-relaxation and, therefore, bring about a cross-peak.

A second inter-nOe interaction was detected and determined to result from the interaction of H-1 of the α-6d-gulo-Hepp unit (δ 5.147) and the H-3 residue of the α-Araf unit (δ 4.148) (FIG. 6). By comparison to the previous interaction, however, the H-1(α-6d-gulo-Hepp) to H-3 (α-Araf) interaction appears significantly weaker. With respect to the proposed structure of linkage in the polysaccharide chain (FIG. 6 (c)), the weaker interaction likely arose from increased distance between the two protons under consideration.

By using both chemical and spectroscopic analysis methodology, it was determined that the oligosaccharide repeat of *C. jejuni* PG2887 (ATCC No. 43442)(HS:15) was [→3)-α-Araf(1→3)-α-6d-gulo-Hepp(1→]$_n$. The *Campylobacter* species has been noted to contain 6d-Hep saccharides in unique ring configurations in previous studies (Monteiro, et al., Infect. Immun., 77: 1128 (2009); Chen, et al., Carbohyd. Res. 243: 1034 (2008); Aspinall, et al., Carbohydr. Res., 279: 227-244 (1995); Aspinall, et al., Carbohydr. Res., 231: 13 (1992)). The 6d-gulo-Hepp saccharide unit found to be present in the CPS of *C. jejuni* PG2887 (ATCC No. 43442) (HS:15) represents a novel find for this species.

Although structural analysis of the CPS of HS15 did not contain MeOPN, it is hypothesized that the [→3)-α-Araf (1→3)-α-6d-gulo-Hepp(1→]$_n$ contains this structure on Hepp. DNA sequence analysis of the capsule locus of the type strain of HS15 revealed the presence of genes for the synthesis of MeOPN. Thus, the type strain of HS15 contains homologs of Cj415, Cj1416, Cj1417 and Cj1418. These genes have been shown to be required for synthesis of MeOPN in *C. jejuni* NCTC 11168 (McNally, et al., J. Biol. Chem. 282:28566-28576 (2007)). Moreover, there is also a putive MeOPN transferase that may be responsible for transfer of the MeOPN to a sugar in the capsule. The MeOPN transferase in the type strain of HS15 is phase varied out of the frame following a homopoymeric tract of GC residues. This may explain why no MeOPN was observed on the capsule structure. However, the putative MeOPN transferase was PCR amplified from 6 other strains of the HS15 serotype and in 5 cases, the MeOPN transferase was in frame. Therefore, the HS15 polysaccharide capsule may or may not be decorated with MeOPN modifications.

*Campylobacter jejuni* strain HS: 10

Monosaccharide Composition and Linkage Analysis of the *Campylobacter jejuni* HS:10 CPS by GC/MS The monosaccharide composition analysis performed on the CPS of *C. jejuni* strain ATCC No. 43438 (HS:10) revealed that it was composed of N-acetyl-galactosamine (GalNAc) and a 6-deoxy-heptose (6d-Hep) (FIG. 7). The careful comparison between the alditol acetate derivative of a synthetically generated 6-d-galacto-heptose and that of the HS:10 CPS, revealed that the 6d-Hep of *C. jejuni* HS10 ATCC No. 43438 CPS possessed the galacto configuration (6d-galacto-Hep). Sugar linkage analysis (FIG. 8) showed that the 6d-galacto-Hep was present as a 3-substituted unit [→3)-6d-Hep-(1→] and that the GalNAc was present as a 3,4-disubstituted residue [→3,4)-GlcNAc-(1→]. Also detected, but in very low amounts, were terminal 6d-gal-Hep [6d-Hep-(1→].

NMR Spectroscopic Analysis of the *Campylobacter jejuni* HS:10 CPS

The $^1$H NMR spectrum (FIG. 9) of the *C. jejuni* ATCC No. 43438 CPS showed three anomeric signals at 5.331, 4.997 and 4.814. The $^1$H NMR spectrum also revealed one singlet at 2.094 assignable to the N-acetyl moiety of GalNAc, and the methylene signals (multiplets) at 1.872 and 1.643 belonging to the 6-deoxy moiety of 6d-galacto-Hep. The $^{31}$P NMR spectrum (FIG. 10) or the CPS showed resonances at 14.113 for O-methyl phosphoramidate (MeOPN).

Sugar Linkage Analysis

In order to place the MeOPN unit within the HS:10 CPS structure, the CPS was treated with 5% acetic acid to selectively remove the MeOPN. Sugar linkage analysis after the acetic acid treatment revealed that the 3-substituted 6-deoxy-galacto-heptose was present in lower amounts and that terminal 6-deoxy-galacto-heptose was now a prominent linkage in the CPS. We thus concluded that the MeOPN was attached at the O-3 position of the 3-substituted 6-deoxy-galacto-heptose.

With the intent of defining the backbone of the HS:10 CPS, the acetic acid treated CPS was subjected to a Smith degradation to selectively remove the terminal 6-deoxy-galacto-heptose from the branched 3,4-linked GalNAc unit. The sugar linkage analysis of the Smith Degradation product showed the appearance of a new 3-linked GalNAc, which pointed to the fact that the branching 6-deoxy-galacto-heptose was attached at the O-4 position of the 3,4-linked GalNAc and that the backbone of the CPS was a 3-linked GalNAc.

The composition and structure of *C. jejuni* serotype HS:10 was deduced to be composed of a GalNAc backbone with branched of 6-deoxy-galacto-heptose that carried a MeOPN at the O-3 position:

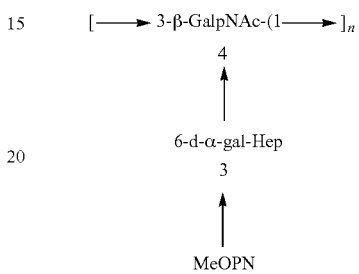

*Campylobacter jejuni* Strain HS: 13

Monosaccharide Composition and Linkage Analysis of the *Campylobacter jejuni* HS:13 CPS by GC/MS The monosaccharide composition analysis performed on the CPS of *C. jejuni* serotype HS:13 revealed that it was composed of glucose (Glc), 6-deoxy-ido-heptose (6d-ido-Hep) and L-glycero-D-ido-heptose (LD-ido-Hep) (FIG. 11). Sugar linkage analysis showed that the Glc was present as a 4-substituted unit and that the 6d-ido-Hep and LD-ido-Hep were present as 3- and 3,7-linked units. Some 2,3-linked hep units were also observed.

NMR Spectroscopic Analysis of the *Campylobacter jejuni* HS:13 CPS

The $^1$H NMR spectrum (FIG. 12) of the *C. jejuni* CPS showed one beta anomeric signal at 4.63 ppm for glucose, and at 4.90 and 4.92 for the heptose units. The $^1$H NMR spectrum also revealed the methylene signals (multiplets) at 1.872 and 1.643 belonging to the 6-deoxy moiety of 6d-ido-Hep. The $^{31}$P NMR spectrum (FIG. 13) of the CPS showed two resonances at ~14 ppm for O-methyl-phosphoramidate units (MeOPN).

Sugar Linkage Analysis Results of *Campylobacter jejuni* HS:13 CPS after Acetic Acid Treatment to Deduce Location of MeOPN In order to place the MeOPN unit within the HS:13 CPS structure, the CPS was treated with 5% acetic acid to selectively remove the MeOPN. Sugar linkage analysis after the acetic acid treatment revealed that 3-substituted 6-deoxy-ido-heptose and L-glycero-ido-heptose were now dominant, which showed that MeOPN was located at O-2 and O-7 of the heptose residues:

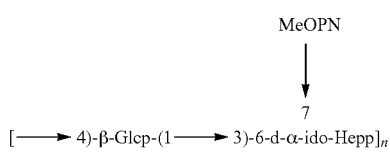

In some disaccharide repeats the 6-deoxy-ido-heptose is replaced by a L-glycero-D-ido-heptose (LD-ido-Hep).

Example 1

Conjugation of *C. jejuni* CPS Carbohydrate Structures to Carrier Molecules

Since IgG response is often predominantly observed as a T-cell independent immune response. Therefore, children are typically only capable of mounting an IgM response in the face of polysaccharide antigens with adults capable of generating an IgG, IgA and IgM response.

In order to potentially further improve the immune response to capsule moieties, it is contemplated that the inventive carbohydrate structures can be conjugated to carrier proteins. Illustrative examples of potential carriers include cross reacting material 197 ($CRM_{197}$) and tetanus toxoid. However, any protein carrier capable of eliciting improved immune response is contemplated.

In a preferred embodiment, conjugation is carried out by reductive amination of the oxidized non-reducing end of the inventive carbohydrate polymer. As an illustration, the isolated arabinose containing carbohydrate polymer of the *C. jejuni* strain HS:15 is conjugated to a protein by first oxidizing the non-reducing end arabinose with periodate to create an aldehyde functional group. Subsequently, the oxidized arabinose is conjugated to the protein carrier by reductive amination. This method is illustrated in FIG. 14. Similarly, also illustrated in FIG. 14, the 6-d-α-gal-Hep of *C. jejuni* strain HS:10 is conjugated to a protein by first oxidizing a 6-d-α-Hep, that is not carrying a MeOPN moiety, with periodate. The oxidized polymer is then conjugated to protein by reductive amination.

Example 2

Prophetic Example of Induction of Immunity Using Capsular Structures

An aspect of this invention is the ability of one or more of the inventive carbohydrate polymers, isolated away from other *Campylobacter* bacterial constituents, to induce an immune response in mammals, such as humans. A further aspect of this invention is that Guillain Barre Syndrome is not induced concomitant to immune induction.

The immunogenic composition contemplated comprises polysaccharide structures from a single or multiple *C. jejuni* strains, selected from the group consisting of HS:10; HS:13; and HS:15. As such, it is anticipated that a limited amount of experimentation is required to ascertain the optimal effective dose ranges, depending on final delivery formulation, carrier and route of administration. However, in a prophetic method for the induction of anti-*C. jejuni* diarrheal protective immunity, a formulation comprising one or more of the following structures would be administered:

1) $[\rightarrow 3)\text{-}\alpha\text{-Araf-}(1\rightarrow 3)\text{-}6\text{-d-}\alpha\text{-gulo-Hepp-}(1\rightarrow]_n$;
    or 2) 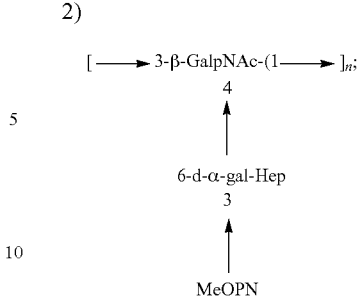

or

3) 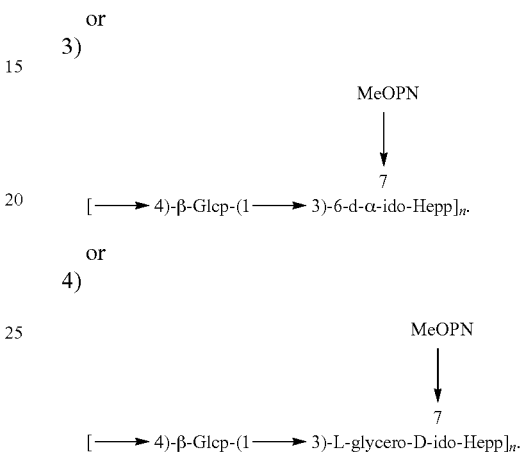

or

4)

$$\text{MeOPN} \downarrow 7$$
$[\longrightarrow 4)\text{-}\beta\text{-Glcp-}(1\longrightarrow 3)\text{-L-glycero-D-ido-Hepp}]_n.$ In another embodiment, the structure $[\rightarrow 3)\text{-}\alpha\text{-Araf-}(1\rightarrow 3)\text{-}6\text{-d-}\alpha\text{-gulo-Hepp-}(1\rightarrow]_n$ contains MeOPN on the Hepp. Furthermore, in a preferred embodiment, the structures are either individually conjugated to a carrier molecule, such as a protein carrier or, alternatively, multiple carbohydrates are conjugated to the same carrier. Although a number of carriers are contemplated, examples of carriers include $CRM_{197}$ and tetanus toxoid. However, any carrier that is capable of enhancing the induction of an immune response is contemplated.

The immunogenic formulation can be administered orally, nasally, subcutaneously, intradermally, transdermally, transcutaneously intramuscularly, or rectally. Depending on the route of administration, the vaccine formulation can be administered with or without any of a number of adjuvants, including but not limited to LTR 192G, Aluminum hydroxide, RC529E, QS21, E294, oligodeoxynucleotides (ODN), CpG-containing oligodeoxynucleotides, aluminum phosphate, MPL® (GlaxoSmithKline, Middlesex, UK) or combinations of these or other potential adjuvants.

It is contemplated that the range of a unit dose of immunogen will be 0.1 μg to 10 mg of immunogen in a range of buffer solutions. In addition, another embodiment is the administration of one or more of the above carbohydrate structures followed by a boosting administration of 1 to 4 doses of one or more of the same structures. In this embodiment, it is contemplated that the unit dose of the boost will range from 0.1 μg to 10 mg of immunogen in a buffered aqueous solution with or without adjuvant.

As mentioned earlier, the carbohydrate structures are contemplated to be administered in conjunction with a carrier molecule, such as a protein. It is contemplated that the carbohydrates would be conjugated individually to the carrier. However, in another embodiment, one or more carbohydrates can be attached to the same carrier molecule.

Obviously, many modifications and variations of the present invention are possible in light of the above teachings.

It is therefore to be understood that, within the scope of the appended claims, the invention may be practiced otherwise than as specifically described.

What is claimed is:

1. An immunogenic composition, composed of one or more of an isolated capsule carbohydrate polymer, wherein the composition does not contain lipooligosaccharides and wherein said capsule carbohydrate polymer is derived from *Campylobacter jejuni* steins HS10 and HS15 and wherein said capsule carbohydrate polymer comprises the formula selected from the group consisting of:

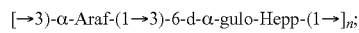

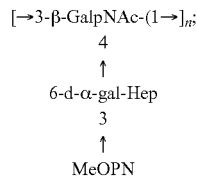

and wherein the capsule carbohydrate polymer is attached to a protein carrier molecule.

2. The immunogenic composition of claim 1, wherein said [→3)-α-Araf-(1→3)-6-d-α-gulo-Hepp-(1→]$_n$ contains MeOPN on the Hepp.

3. The immunogenic composition of claim 1, wherein the carbohydrate polymer structure [→3)-α-Araf-(1→3)-6-d-α-gulo-Hepp-(1→]$_n$ is conjugated to a carrier molecule via Arabinose.

4. The immunogenic composition of claim 1, wherein the carbohydrate polymer

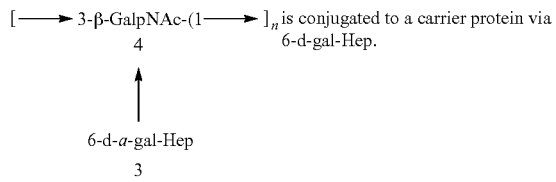

MeOPN

5. The immunogenic composition of claim 1, wherein said protein carrier molecule is cross reacting material 197 (CRM$_{197}$) or tetanus toxoid.

6. An immunogenic composition of claim 1, wherein said composition also comprises one or both of the capsule carbohydrate polymers derived from the *C. jejuni* strain HS13, comprising the structure:

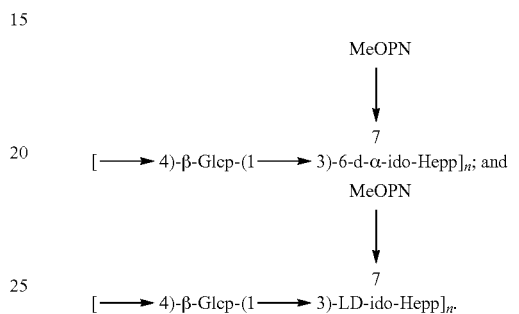

7. A method of inducing an immune response against *Campylobacter jejuni* immunity comprising administering the composition of claim 1 to a mammal.

8. The method of claim 7, wherein said immunogenic composition can be administered orally, nasally, subcutaneously, intradermally, transdermally, transcutaneously intramuscularly, or rectally.

9. The method of claim 7, wherein said immunogenic composition is administered with an adjuvant.

10. The method of claim 7, wherein said adjuvant is selected from the group consisting of LTR 192G, Aluminum hydroxide, RC529E, QS2L E294, oligodeoxynucleotides (QDN), CpG-containing oligodeoxynucleotides, and aluminum phosphate.

11. The method of claim 7, wherein said carrier is CRM197 or tetanus toxoid.

* * * * *